(12) United States Patent
Satoh et al.

(10) Patent No.: US 6,433,174 B1
(45) Date of Patent: Aug. 13, 2002

(54) PROCESS FOR PRODUCING NOVEL NAPHTHYRIDINE DERIVATIVES

(75) Inventors: Yoshitaka Satoh, Yoshikawa; Makoto Tsuda, Tokyo; Masashi Nagai, Tanashi; Hiroko Yamazaki, Tokyo, all of (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/831,860

(22) PCT Filed: Dec. 15, 1999

(86) PCT No.: PCT/JP99/07049

§ 371 (c)(1),
(2), (4) Date: May 15, 2001

(87) PCT Pub. No.: WO00/35918

PCT Pub. Date: Jun. 22, 2000

(30) Foreign Application Priority Data

Dec. 16, 1998 (JP) .............................. 10-357240
Feb. 16, 1999 (JP) .............................. 11-036798

(51) Int. Cl.[7] ........................................ C07D 471/04
(52) U.S. Cl. .................... 546/81; 546/88; 546/122
(58) Field of Search ...................... 546/81, 88, 122

(56) References Cited

FOREIGN PATENT DOCUMENTS

| EP | 0 319 429 | 7/1989 |
|---|---|---|
| JP | 3-2166 | 1/1991 |
| WO | 99/00388 | 1/1999 |

*Primary Examiner*—Bernard Dentz
(74) *Attorney, Agent, or Firm*—Nields & Lemack

(57) ABSTRACT

A novel naphthyridine derivative showing high activity as a tachykinin receptor antagonist can be produced at high efficiency by reacting an acylating agent such as a carboxylic acid derivative with a compound represented by the formula (1):

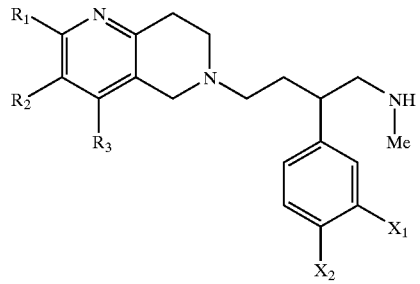

(1)

wherein $R_1$, $R_2$ and $R_3$ represent independently a hydrogen atom, a lower alkyl group, a lower alkoxyl group, an aryl group, a heteroaryl group, an amino group, etc., and $X_1$ and $X_2$ represent respectively a halogen atom.

8 Claims, No Drawings

PROCESS FOR PRODUCING NOVEL NAPHTHYRIDINE DERIVATIVES

This application is a 371 of PCT/JP99/07049, filed Dec. 15, 1999.

TECHNICAL FIELD

The present invention relates to a process for producing novel naphthyridine derivatives having an antagonistic action against tachykinin receptors, especially neurokinin A receptor (NK-2 receptor), intermediates used in this process, and a process for producing such intermediates.

BACKGROUND ART

The compounds acting antagonistically to various types of tachykinin receptors have been reported. For instance, JP-A-4-261155 discloses a compound having an antagonistic action against neurokinin receptors (especially NK-2 receptor). Further, JP-A-5-140103 describes a compound which antagonizes against substance P, neurokinin A or neurokinin B receptor. These compounds have a single ring containing a nitrogen atom, such as a piperidine ring, in the molecule, but no compound having a naphthyridine ring has ever been disclosed.

Regarding the compounds having a naphthyridine ring, JP-A-58-57379 discloses a compound having an antivertiginous action. However, it has never been reported that these compounds having a naphthyridine ring have an antagonistic action against tachykinin receptors.

DISCLOSURE OF THE INVENTION

The present invention is designed to provide a process for producing the novel naphthyridine derivatives showing a high activity as a tachykinin receptor antagonist, intermediates used in this process, and a process for producing such intermediates.

As a result of extensive studies on the subject matter, the present inventors found that the novel naphthyridine derivatives having a naphthyridine ring as the basic skeleton have a prominent antagonistic action against tachykinin receptors and are well applicable as pharmaceuticals. The present inventors have also pursued studies on the way of production of these derivatives and worked out a production process which can well withstand its industrial application. These findings underlie the present invention.

The novel naphthyridine derivatives of the present invention have the asymmetric carbon atoms, so that they exist as a single optically active compound or a racemate thereof, and each of them has an outstanding activity as a tachykinin receptor antagonist. Also, part of the novel naphthyridine derivatives of the present invention can be used as an intermediate for the synthesis of the other part of the naphthyridine derivatives of the present invention.

The optically active compounds comprising the novel naphthyridine derivatives of the present invention can be easily obtained as required by, for instance, optically resolving their intermediates. A diastereomer salt produced by acting an optically active amine to a racemate of the synthesis intermediate can be optically resolved by, for instance, a method making use of the difference in their physicochemical properties. Further, by using an isomeric crystallization method, it is possible to obtain an objective optically active product of the intermediate in a higher yield than obtainable with ordinary optical resolution. Using such optically active substances, it is possible to obtain the optically active compounds comprising the novel naphthyridine derivatives of the present invention at high efficiency.

The present invention has been achieved on the basis of the above findings.

Thus, the present invention provides:

(i) A process for producing a novel naphthyridine derivative, which comprises carrying out a condensation reaction between a compound represented by the following formula (1):

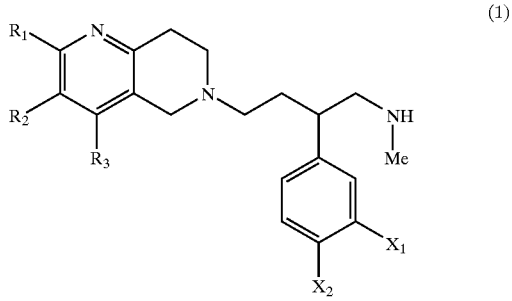

wherein $R_1$, $R_2$ and $R_3$ represent independently a hydrogen atom, a lower alkyl group, a lower alkoxyl group, an aryl group, a heteroaryl group, an amino group or a halogen atom, or $R_1$ and $R_2$ or $R_2$ and $R_3$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, aryl group, heteroaryl group, lower alkoxyl group, halogen atom and trifluoromethyl group; and $X_1$ and $X_2$ represent respectively a halogen atom, and a compound represented by the following formula (2):

wherein Y represents an aryl group which may have 1 to 3 substituents selected from halogen atom and lower alkoxyl group; and Z represents a halogen atom, a hydroxyl group, a lower alkylcarbonyloxy group or an arylcarbonyloxy group, to produce a compound represented by the following formula (3):

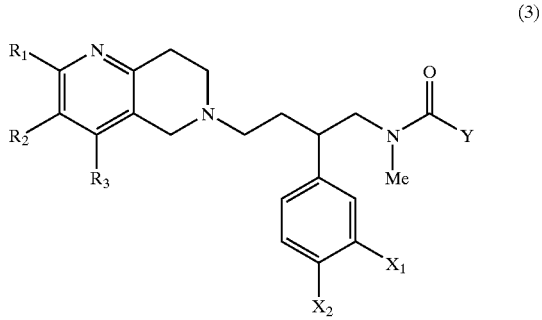

wherein $R_1$, $R_2$, $R_3$, $X_1$, $X_2$ and Y have the same meaning as defined above.

(ii) The process described in (i) above, wherein in the formula (1), $R_1$ and $R_2$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, lower alkoxyl group, halogen atom, aryl group, heteroaryl group and trifluoromethyl group; and $R_3$ represents a hydrogen atom, a lower alkyl group, a lower alkoxyl group, an aryl group, an amino group or a halogen atom.

(iii) The process described in (i) above, wherein in the formula (1), $R_1$ and $R_2$ are combined to form a cyclic group with the interposition of a C2–C5 alkylene group or a C2–C5 alkenylene group, which cyclic group may have a substituent selected from lower alkyl group, lower alkoxyl group, halogen atom and trifluoromethyl group; $R_3$ represents a hydrogen atom, a lower alkyl group, a lower alkoxyl group, an aryl group, an amino group or a halogen atom; and in the formula (2), Y represents a phenyl group which may have 1 to 3 substituents selected from halogen atom and lower alkoxyl group.

(iv) The process described in (i) above, wherein in the formula (1), $R_1$ and $R_2$ are combined to form a cyclic group with the interposition of a butylene group or a butenylene group; $R_3$ represents a hydrogen atom, an aryl group, an amino group or a halogen atom; and in the formula (2), Y represents a phenyl group.

(v) A process for producing a novel naphthyridine derivative, which comprises acylating the amino group of a compound represented by the following formula (3)':

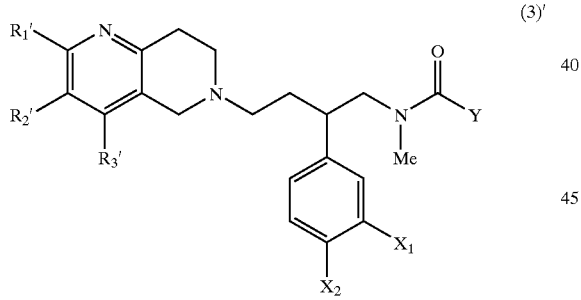

wherein $R_1'$, $R_2'$ and $R_3'$ represent independently a hydrogen atom, a lower alkyl group, a lower alkoxyl group, an aryl group, a heteroaryl group, an amino group or a halogen atom, or $R_1'$ and $R_2'$ or $R_2'$ and $R_3'$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, aryl group, heteroaryl group, lower alkoxyl group, halogen atom and trifluoromethyl group, and at least one of $R_1'$, $R_2'$ and $R_3'$ is an amino group; $X_1$ and $X_2$ represent respectively a halogen atom; and Y represents an aryl group which may have 1 to 3 substituents selected from halogen atom and lower alkoxyl group, to produce a compound represented by the formula (3)":

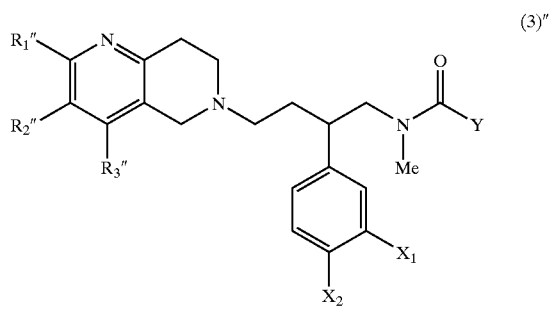

wherein $R_1''$, $R_2''$ and $R_3''$ represent independently a hydrogen atom, a lower alkyl group, a lower alkoxyl group, an aryl group, a heteroaryl group or a halogen atom, or $R_1''$ and $R_2''$ or $R_2''$ and $R_3''$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, aryl group, heteroaryl group, lower alkoxyl group, halogen atom and trifluoromethyl group, and at least one of $R_1''$, $R_2''$ and $R_3''$ is a lower alkylcarbonylamino group or an arylcarbonylamino group; and $X_1$, $X_2$ and Y have the same meaning as defined above.

(vi) The process described in (v) above, wherein in the formula (3)', $R_1'$ and $R_2'$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, aryl group, heteroaryl group, lower alkoxyl group, halogen atom and trifluoromethyl group; $R_3'$ represents an amino group; and in the formula (3)", $R_1''$ and $R_2''$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, aryl group, heteroaryl group, lower alkoxyl group, halogen atom and trifluoromethyl group; and $R_3''$ represents a lower alkylcarbonylamino group or an arylcarbonylamino group.

(vii) The process described in (v) above, wherein in the formula (3)', $R_1'$ and $R_2'$ are combined to form a cyclic group with the interposition of a C2–C5 alkylene group or a C2–C5 alkenylene group, which cyclic group may have a substituent selected from lower alkyl group, lower alkoxyl group, halogen atom and trifluoromethyl group; $R_3'$ represents an amino group; Y represents a phenyl group which may have 1 to 3 substituents selected from halogen atom and lower alkoxyl group; and in the formula (3)", $R_1''$ and $R_2''$ are combined to form a cyclic group with the interposition of a C2–C5 alkylene group or a C2–C5 alkenylene group, which cyclic group may have a substituent selected from lower alkyl group, lower alkoxyl group, halogen atom and trifluoromethyl group; and $R_3''$ represents a lower alkylcarbonylamino group.

(viii) The process described in (v) above, wherein in the formula (3)', $R_1'$ and $R_2'$ are combined to form a cyclic group with the interposition of a butylene group or a butenylene group; $R_3'$ represents an amino group; Y represents a phenyl group; and in the formula (3)", $R_1''$ and $R_2''$ are combined to form a cyclic group with the interposition of a butylene group or a butenylene group; and $R_3''$ represents a lower alkylcarbonylamino group.

(ix) Racemates, optical active products or salts of the 3-(3,4-dihalogenophenyl)propionic acid derivatives represented by the following formula (4):

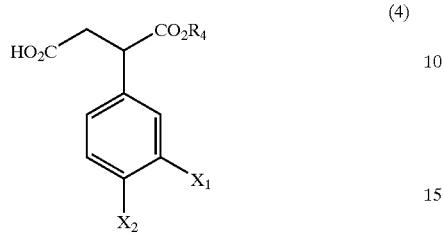

(4)

wherein $X_1$ and $X_2$ represent respectively a halogen atom; and $R_4$ represents a C1–C20 hydrocarbon residue which may have a substituent and in which an oxygen, nitrogen or sulfur atom may exist.

(x) The compounds described in (ix) above, wherein $X_1$ and $X_2$ represent respectively a chlorine atom; and $R_4$ represents a C1–C5 alkyl group which may be substituted with an aryl group.

(xi) The compounds described in (ix) or (x) above, which are the salts with an optically active amine.

(xii) The compounds described in (xi) above, wherein the optically active amine is 1-arylethylamine which may have a substituent.

(xiii) The compounds described in (xii) above, wherein the optically active amine is (S)- or (R)-1-phenylethylamine, (S)- or (R)-1-(p-tolyl)ethylamine, (s)- or (R)-1-(1-naphthyl)ethylamine, (S)- or (R)-1-phenyl-2-(p-tolyl)ethylamine or (S)- or (R)-N-benzyl-1-phenylethylamine.

(xiv) A process for producing an optically active 3-(3,4-dihalogenophenyl)propionic acid derivative, which comprises acting an optically active amine to a racemate of a 3-(3,4-dihalogenophenyl)propionic acid derivative represented by the formula (4):

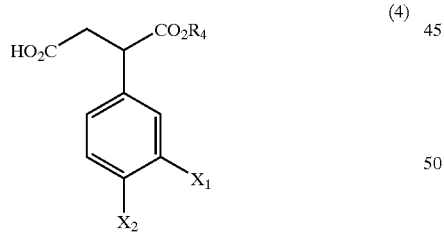

(4)

wherein $X_1$ and $X_2$ represent respectively a halogen atom; and $R_4$ represents a C1–C20 hydrocarbon residue which may have a substituent and in which an oxygen, nitrogen or sulfur atom may exist, optically resolving the produced diastereomer salt, and decomposing the obtained optically active diastereomer salt.

(xv) The process described in (xix) above, wherein $X_1$ and $X_2$ represent respectively a chlorine atom; and $R_4$ represents a C1–C5 alkyl group which may be substituted with an aryl group.

(xvi) The process described in (xiv) or (xv) above, wherein the optically active amine is 1-arylethylamine which may have a substituent.

(xvii) The process described in (xvi) above, wherein the optically active amine is (S)- or (R)-1-phenylethylamine, (S)- or (R)-1-(p-tolyl)ethylamine, (S)- or (R)-1-(1-naphthyl)ethylamine, (S)- or (R)-1-phenyl-2-(p-tolyl)ethylamine, or (S)- or (R)-N-benzyl-1-phenylethylamine.

(xviii) A process for producing a 3-(3,4-dihalogenophenyl)propionic acid derivative, which comprises carrying out an alkylation reaction with a compound epresented by the formula (5):

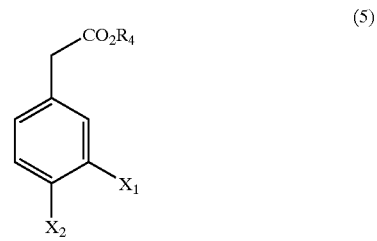

(5)

wherein $X_1$ and $X_2$ represent respectively a halogen atom; and $R_4$ represents a C1–C20 hydrocarbon residue which may have a substituent and in which an oxygen, nitrogen or sulfur atom may exist, to obtain a compound represented by the formula (4):

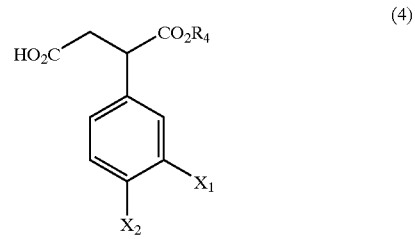

(4)

wherein $X_1$ and $X_2$ represent respectively a halogen atom; and $R_4$ represents a C1–C20 hydrocarbon residue which may have a substituent and in which an oxygen, nitrogen or sulfur atom may exist.

(xix) The process described in (xviii) above, wherein the compound is treated with an alkaline metal halogenoacetate in an aprotic polar solvent in the presence of a strong base at a temperature from −40° C. to +25° C.

(xx) A process for producing an amine compound, which comprises reacting a compound represented by the formula (6):

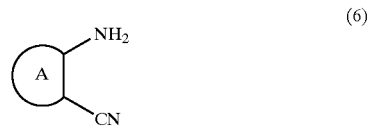

(6)

wherein A represents a benzene ring which may have a substitutent selected from lower alkyl group, lower alkoxyl group, aryl group, heteroaryl group, amino group, halogen atom and trifluoromethyl group, with a compound represented by the formula (7):

(7)

wherein $R_5$ represents a methyl group which may be substituted with a lower alkyl group or an aryl group in the presence of a reacting agent represented by the formula (8):

(8)

wherein $R_6$, $R_7$ and $R_8$ represent independently a lower alkyl group or an aryl group; and Z represents a halogen atom or a fluorinated alkyl sulfonate, to produce a compound represented by the formula (9):

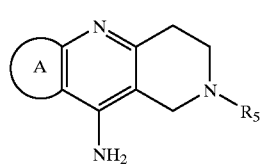

(9)

wherein A and $R_5$ are as defined above.

(xxi) The process described in (xx) above, wherein in the formula (6), A represents a benzene ring substituted with a hydrogen atom, a halogen atom or a lower alkyl group; in the formula (7), $R_5$ represents a methyl group or a benzyl group; and in the formula (8), $R_6$, $R_7$ and $R_8$ represent independently a methyl group, an ethyl group, an isopropyl group, a tert-butyl group or a phenyl group, and Z represents bromine, iodine, trifluoromethane sulfonate, pentafluoroethane sulfonate, pentafluoro-n-propane sulfonate or nanofluoro-n-butane sulfonate.

(xxii) The process described in (xxi) above, wherein in the formula (6), A represents a non-substituted benzene ring; in the formula (7), $R_5$ represents a benzyl group; and in the formula (8), $R_6$, $R_7$ and $R_8$ represent a methyl group, and Z represents bromine, iodine or trifluoromethane sulfonate.

BEST MODE FOR CARRYING OUT THE INVENTION

In the naphthyridine derivatives according to the present invention, the lower alkyl group is preferably a C1–C4 linear or branched alkyl group such as methyl, ethyl, n-propyl, isopropyl, n-butyl, sec-butyl and tert-butyl. Of these groups, methyl and ethyl are preferred.

The lower alkoxyl group in the derivatives of the present invention is preferably a C1–C4 linear or branched alkoxyl group such as methoxy, ethoxy, n-propoxy, isopropoxy, n-butoxy, isobutoxy and tert-butoxy. Of these groups, methoxy and ethoxy are preferred.

The halogen atom in the derivatives of the present invention is fluorine atom, chlorine atom, bromine atom or iodine atom, of which chlorine atom is preferred.

The aryl group in the derivatives of the present invention is preferably a C6–C14 aryl group such as phenyl, biphenyl, naphthyl, anthryl and phenanthryl, of which phenyl and naphthyl are preferred.

The heteroaryl group in the derivatives of the present invention is preferably an unsaturated 5- to 7-member ring containing 1 to 5, preferably 1 to 2 hetero-atoms selected from nitrogen atom, oxygen atom and sulfur atom, such as thienyl, imidazolyl, pyridinyl, pyridiminyl and pyridazinyl.

The C2–C5 alkylene group in the derivatives of the present invention is, for instance, ethylene, propylene, butylene or pentylene.

The C2–C5 alkenylene group in the derivatives of the present invention is, for instance, ethynylene, propenylene, butynylene or pentenylene.

The lower alkylcarbonyloxy group in the derivatives of the present invention is a group comprising a lower alkyl group such as mentioned above to which a carbonyloxy group is attached.

The arylcarboxyloxy group in the derivatives of the present invention is a group comprising an aryl group such as mentioned above to which a carbonyloxy group is attached.

The hydrocarbon residue in the derivatives of the present invention is preferably a C2–C5 alkylene group, a C2–C5 alkenylene group, a C6–C14 aryl group, such as mentioned above, or the like.

In the formulae (1) and (3), preferably $R_1$ and $R_2$ are combined to form a cyclic group with the interposition of a saturated or unsaturated carbon-carbon bond. This cyclic group may contain 1 to 3 hetero-atoms selected from nitrogen atom, oxygen atom and sulfur atom and may also have a substituent selected from lower alkyl group, lower alkoxyl group, aryl group, heteroaryl group, halogen atom and trifluoromethyl group. $R_3$ in these formulae is preferably a hydrogen atom, a lower alkyl group, a lower alkoxyl group, an aryl group, an amino group or a halogen atom. More preferably, $R_1$ and $R_2$ are combined to form a cyclic group with the interposition of a C2–C5 alkylene group or a C2–C5 alkenylene group, which cyclic group may have a substituent such as mentioned above. Most preferably, $R_1$ and $R_2$ are combined to form a cyclic group with the interposition of a butylene or butenylene group, and $R_3$ is a hydrogen atom, an aryl group, an amino group or a halogen atom.

In the formula (3)', preferably $R_1'$ and $R_2'$ are combined to form a cyclic group which may contain 1 to 3 hetero-atoms selected from nitrogen atom, oxygen atom and sulfur atom, with the interposition of a saturated or unsaturated carbon-carbon bond. This cyclic group may also have a substituent selected from lower alkyl group, lower alkoxyl group, halogen atom and trifluoromethyl group. $R_3'$ is preferably an amino group. More preferably, $R_1'$ and $R_2'$ are combined to form a cyclic group with the interposition of a C2–C5 alkylene group or a C2–C5 alkenylene group, which cyclic group may have a substituent selected from lower alkyl group, lower alkoxyl group, halogen atom and trifluoromethyl group. Most preferably, $R_1'$ and $R_2'$ are combined to form a cyclic group with the interposition of a butylene or butenylene group.

In the formula (3)", $R_1"$ and $R_2"$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, lower alkoxyl group, aryl group, heteroaryl group, halogen atom and trifluoromethyl group. $R_3"$ is preferably a lower alkylcarbonylamino group or an arylcarbonylamino group. More preferably, $R_1"$ and $R_2"$ are combined to form a cyclic group with the interposition of a C2–C5 alkylene group or a C2–C5 alkenylene group, which cyclic group may have a substituent selected from lower alkyl group, lower alkoxyl group, halogen atom and trifluoromethyl group. $R_3"$ is preferably a lower alkyl-carbonylamino group. Most preferably, $R_1"$ and $R_2"$ are combined to form a cyclic group with the interposition of a butylene or butenylene group, and $R_3"$ is a lower alkylcarbonylamino group.

The hydrocarbon residue represented by $R_4$ in the formulae (4) and (5) is the one whose carbon number is preferably from 1 to 10, more preferably from 1 to 5. The substituents of this hydrocarbon residue include C1–C5 alkoxyl group, nitro group, halogen and aryl group, preferably C1–C5 alkoxyl group. Preferred examples of $R_4$ are methyl, ethyl, propyl, butyl and benzyl. Practically, methyl, ethyl and benzyl are preferred.

In the formulae (2), (3) and (3)', preferably Y is a phenyl group which may have 1 to 3 substituents selected from halogen atom and lower alkoxyl group, more preferably a phenyl group.

In the formulae (6) and (9), A represents a benzene ring whose substituent is selected from lower alkyl group, lower alkoxyl group, aryl group, heteroaryl group and halogen atom, the examples of which are the same as mentioned above. The preferred substituents are halogen atom and lower alkyl group. Most preferably, A is a non-substituted benzene ring.

In the formula (7), $R_5$ is preferably a methyl group substituted with an aryl group, most preferably a benzyl group.

In the formula (8), preferably $R_6$, $R_7$ and $R_8$ are a methyl group, an ethyl group, an isopropyl group, a tert-butyl group, a phenyl group or the like, and most preferably, all of $R_6$, $R_7$ and $R_8$ are a methyl group.

The halogen atoms represented by Z in the formula (8) are the same as mentioned above. The fluorinated alkyl sulfonates also represented by Z include, for example, trifluoromethane sulfonate, pentafluoroethane sulfonate, heptafluoromethane sulfonate and nanofluoro-n-butane sulfonate. Z is preferably a bromine atom, an iodine atom or trifluoromethane sulfonate.

The compounds represented by the formula (3) include the following:

①-a: (±)-10-amino-2-[4-(N-benzoyl-N-methyl)amino-3-(3,4-dichlorophenyl)butyl]-1,2,3,4,6,7,8,9-octahydrobenzo[b][1,6]-naphthyridine;

①-b: (−)-10-amino-2-[4-(N-benzoyl-N-methyl)amino-3-(3,4-dichlorophenyl)butyl]-1,2,3,4,6,7,8,9-octahydrobenzo[b][1,6]-naphthyridine;

①-c: (+)-10-amino-2-[4-(N-benzoyl-N-methyl)amino-3-(3,4-dichlorophenyl)butyl]-1,2,3,4,6,7,8,9-octahydrobenzo[b][1,6]-naphthyridine;

②-a: (±)-2-[4-(N-benzoyl-N-methyl)amino-3-(3,4-dichlorophenyl)butyl]-1,2,3,4,6,7,8,9-octahydrobenzo[b][1,6]-naphthyridine;

②-b: (−)-2-[4-(N-benzoyl-N-methyl)amino-3-(3,4-dichlorophenyl)butyl]-1,2,3,4,6,7,8,9-octahydrobenzo[b][1,6]-naphthyridine;

②-c: (+)-2-[4-(N-benzoyl-N-methyl)amino-3-(3,4-dichlorophenyl)butyl]-1,2,3,4,6,7,8,9-octahydrobenzo[b][1,6]-naphthyridine;

③-a: (±)-2-[4-(N-benzoyl-N-methyl)amino-3-(3,4-dichorophenyl)butyl]-10-phenyl-1,2,3,4-tetrahydrobenzo[b][1,6]-naphthyridine;

③-b: (−)-2-[4-(N-benzoyl-N-methyl)amino-3-(3,4-dihclorophenyl)butyl]-10-phenyl-1,2,3,4-tetrahydrobenzo[b][1,6]-naphthyridine;

③-c: (+)-2-[4-(N-benzoyl-N-naphthyl)amino-3-(3,4-dichlorophenyl)butyl]-10-phenyl-1,2,3,4-tetrahydrobenzo[b][1,6]-naphthyridine;

④-a: (±)-2-[4-(N-benzoyl-N-methyl)amino-3-(3,4-dichlorophenyl)butyl]-10-chloro-1,2,3,4-tetrahydrobenzo[b][1,6]-naphthyridine;

④-b: (−)-2-[4-(N-benzoyl-N-methyl)amino-3-(3,4-dichlorophenyl)butyl]-10-chloro-1,2,3,4-tetrahydrobenzo[b][1,6]-naphthyridine;

④-c: (+)-2-[4-(N-benzoyl-N-methyl)amino-3-(3,4-dichlorophenyl)butyl]-10-chloro-1,2,3,4-tetrahydrobenzo[b][1,6]-naphthyridine.

The compounds represented by the formula (3)" include the following:

⑤-a: (±)-10-acetylamino-2-[4-(N-benzoyl-N-methyl)-amino-3-(3,4-dichlorophenyl)butyl]-1,2,3,4,6,7,8,9-octahydrobenzo[b][1,6]-naphthyridine;

⑤-b: (−)-10-acetylamino-2-[4-(N-benzoyl-N-methyl)-amino-3-(3,4-dichlorophenyl)butyl]-1,2,3,4,6,7,8,9-octahydrobenzo[b][1,6]-naphthyridine;

⑤-c: (+)-10-acetylamino-2-[4-(N-benzoyl-N-methyl)-amino-3-(3,4-dichlorophenyl)butyl]-1,2,3,4,6,7,8,9-octahydrobenzo[b][1,6]-naphthyridine;

⑥-a: (±)-10-acetylamino-2-[4-(N-benzoyl-N-methyl)-amino-3-(3,4-dichlorophenyl)butyl]-1,2,3,4-tetrahydrobenzo[b][1,6]-naphthyridine;

⑥-b: (−)-10-acetylamino-2-[4-(N-benzoyl-N-methyl)-amino-3-(3,4-dichlorophenyl)butyl]-1,2,3,4-tetrahydrobenzo[b][1,6]-naphthyridine;

⑥-c: (+)-10-acetylamino-2-[4-(N-benzoyl-N-methyl)-amino-3-(3,4-dichlorophenyl)butyl]-1,2,3,4-tetrahydrobenzo[b][1,6]-naphthyridine;

⑦-a: (±)-10-acetylamino-2-[4-(N-benzoyl-N-methyl)-amino-3-(3,4-difluorophenyl)butyl]-1,2,3,4-tetrahydrobenzo[b][1,6]-naphthyridine;

⑦-b: (−)-10-acetylamino-2-[4-(N-benzoyl-N-methyl)-amino-3-(3,4-difluorophenyl)butyl]-1,2,3,4-tetrahydrobenzo[b][1,6]-naphthyridine;

⑦-c: (+)-10-acetylamino-2-[4-(N-benzoyl-N-methyl)-amino-3-(3,4-difluorophenyl)butyl]-1,2,3,4-tetrahydrobenzo[b][1,6]-naphthyridine;

⑧-a: (±)-2-[4-(N-benzoyl-N-methyl)amino-3-(3,4-difluorophenyl)butyl]-10-benzoylamino-1,2,3,4-tetrahydrobenzo[b][1,6]-naphthyridine;

⑧-b: (−)-2-[4-(N-benzoyl-N-methyl)amino-3-(3,4-difluorophenyl)butyl]-10-benzoylamino-1,2,3,4-tetrahydrobenzo[b][1.6]-naphthyridine;

⑧-c: (+)-2-[4-(N-benzoyl-N-methyl)amino-3-(3,4-difluorophenyl)butyl]-10-benzoylamino-1,2,3,4-tetrahydrobenzo[b][1,6]-naphthyridine.

The novel naphthyridine derivatives produced according to the present invention may be used in the form of pharmacologically acceptable salts. Such salts, to be concrete, include the salts with mineral acids such as hydrochloric acid and sulfuric acid, and the salts with organic acids such as acetic acid, lactic acid, succinic acid, fumaric acid, maleic acid, citric acid, benzoic acid, methanesulfonic acid and p-toluenesulfonic acid.

The production processes according to the present invention are described in detail below.

The novel naphthyridine derivatives of the formulae (3) and (3)" of the present invention can be produced according to the conventional synthesis processes illustrated by the following schemes 1 and 2.

Scheme 1

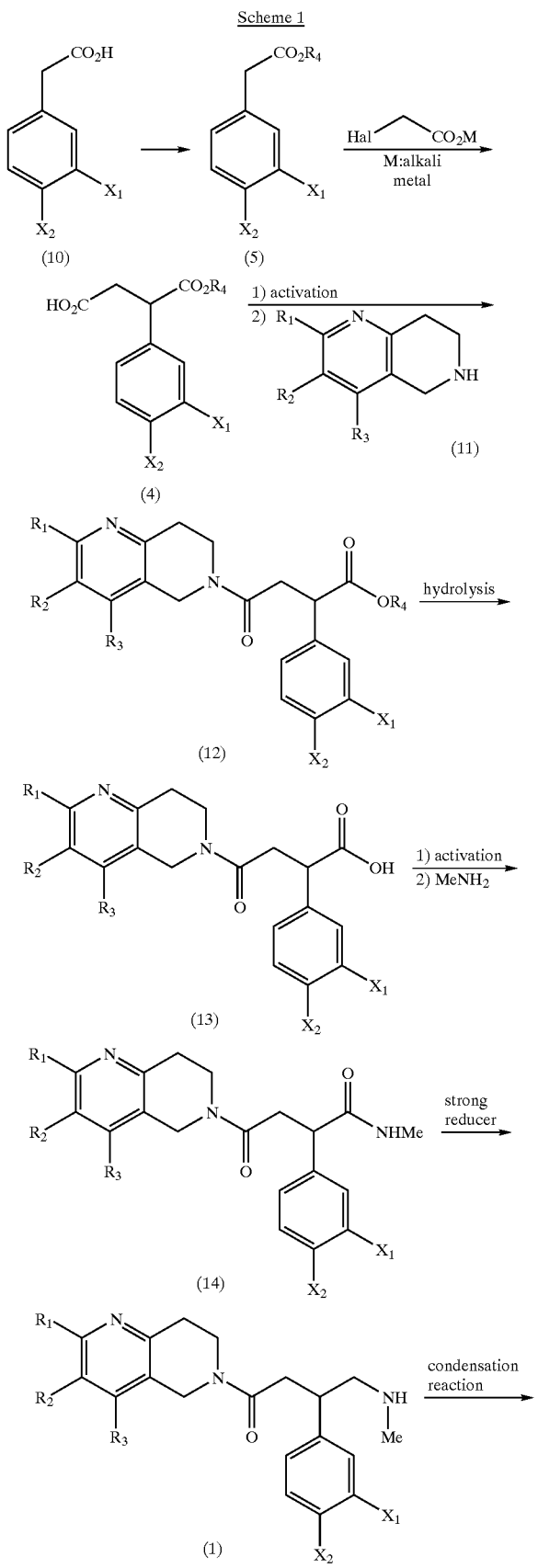

Scheme 2

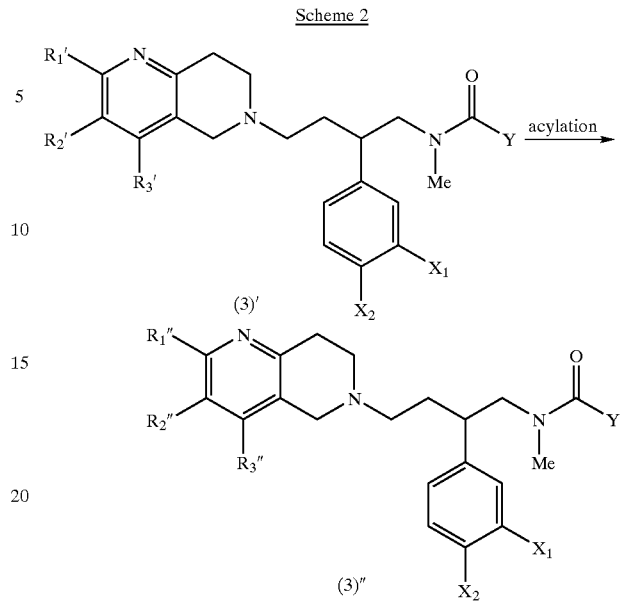

In Scheme 1, the compound represented by the formula (5) can be obtained by reacting a compound of the formula (10), which is easily available from, for example, Tokyo Kasei KK (Tokyo), with a halogenated hydrocarbon compound such as alkyl halide or benzyl halide in a solvent such as an alcohol (methanol, ethanol, etc.), acetone or dimethylformamide in the presence of a basic catalyst such as potassium carbonate, potassium hydroxide or sodium hydroxide under the range of room temperature to solvent-reflux temperature. It is also possible to obtain the compound of the formula (5) by reacting a compound of the formula (10) with a corresponding alcohol compound ($R_4OH$) in a non-alcoholic organic solvent in the presence of an acid catalyst such as sulfuric acid or hydrochloric acid under reflux by heating from room temperature.

The compound of the formula (4) can be obtained by alkylating the compound of the formula (5) with an alkaline metal halogenoacetate in an aprotic polar solvent in the presence of a strong base.

As the aprotic polar solvent, dimethylformamide, dimethyl sulfoxide, N-methylpyrrolidone, 1,3-dimethyl-2-imidazolidinone and the like can be used, but dimethylformamide and dimethyl sulfoxide are preferred, the latter being especially preferred.

As the strong base, sodium hydroxide, sodium tert-butoxide, n-butyllithium, lithium, diisopropylamide, etc., can be used, of which sodium hydroxide and sodium tert-butoxide are preferred, the former being particularly preferred.

As the alkaline metal halogenoacetate, sodium chloroacetate, potassium bromoacetate, etc., can be used, with sodium chlorocetate being preferred.

The reaction can be carried out in a wide temperature range of from −78° C. to 100° C., but practically a temperature from −40° C. to 25° C. is preferably used.

The compound of the formula (4) obtained in the manner described above can be optically resolved as required in the following way.

An optically active amine and a solvent, preferably an isomerization assistant, are added to a (±)-3-(3,4-dihalogenophenyl)propionic acid derivative of the formula (4), and with the amount of the solvent adjusted to allow crystallization of the best part of the diastereomer which is less soluble in said solvent, the mixture is stirred by heating at a temperature of from 50° C. to around the boiling point of the solvent used, preferably at 60° C. to 120° C., for several to several ten hours, accumulating the diastereomer salt which is lower in solvent solubility in the two types of diastereomer salt, then the accumulated diastereomer salt is cooled to −10 to 40° C. and the precipitated hardly soluble salt is separated.

As the optically active amine, it is possible to use any type which is capable of forming a crystallizable salt with the 3-(3,4-dihalogenophenyl)propionic acid derivative of the formula (4). Usually, an easily available basic optical resolving agent is used. In this case, those which are easily racemated with an isomerization assistant described later should be avoided. Examples of the optically active amines usable in the present invention include, as those of the natural origin, quinine, quinidine, cinchonine, cinchonidine, ephedrine, L-lysine, (+)-dehydroabiethylamine and L-alginine. The synthetic products of such optically active amines include (+)- or (−)-1-phenylethylamine, (+)- or (−)-1-(p-tolyl)ethylamine, (+)- or (−)-1-(o-tolyl)ethylamine, (+)- or (−)-1-(m-tolyl)ethylamine, (+)- or (−)-1-(p-nitrophenyl) ethylamine, (+)- or (−)-1-(p-isopropylphenyl)ethylamine, (+)- or (−)-α-ethylbenzylamine, (+)- or (−)-1-(p-chlorophenyl)ethylamine, (+)- or (−)-1-(p-methoxyphenyl) ethylamine, (+)- or (−)-1-(p-nitrophenyl)ethylamine, (+)- or (−)-1-phenyl-2-(p-tolyl)ethylamine, (+)- or (−)-erythro-2-amino-1,2-diphenylethanol, (+)- or (−)-1-(1-naphtyl) ethylamine, (+)- or (−)-1-(2-naphthyl)ethylamine, (+)- or (−)-cis-2-(benzylamino)cyclohexanemethanol, (+)- or (−)-α-methyl-p-nitrobenzylamine, (+)- or (−)-N-benzyl-1-phenylethylamine, and (+)- or (−)-N-(p-nitrobenzyl)-1-phenylethylamine. The optionally substituted (+)- or (−)-α-arylethylamine derivatives are preferably used, with (+)- or (−)-1-phenylethylamine being particularly preferred.

As the solvent, there can usually be used alcohols such as methanol, ethanol, 1-propanol, 2-propanol, 1-butanol and 2-butanol; ketones such as acetone, methyl ethyl ketone, methyl isobutyl ketone, diethyl ketone, di-n-propyl ketone, di-iso-propyl ketone and methyl isopropyl ketone; aromatic hydrocarbons such as benzene, toluene and xylene; ethers such as tetrahydrofuran, dioxane, isopropyl ether, 2-methoxyethyl ether and diethyl ether; hydrocarbons such as hexane, heptane and octane; halogenated hydrocarbons such as chloroform, dichloromethane and 1,2-dichloroethane; esters such as methyl acetate, ethyl acetate and butyl acetate; nitrites such as acetonitrile and propionitrile; water, and suitable combinations of these solvents. Alcohols such as ethanol, 1-propanol, 2-propanol and 1-butanol are preferably used. The amount of the solvent to be used is variable depending on the type of the solvent, the (±)-3-(3,4-dihalogenophenyl)propionic acid derivative and the optically active amine used, but usually an amount is selected that will cause crystallization of the most part of the diastereomer which is less soluble in the solvent. It is approximately 1 to 200 ml, preferably about 2 to 80 ml, per 1 g of the diastereomer salt.

As the isomerization assistant, the amines having stronger basicity than the optically active amine used as the optical resolving agent can be used. Examples of such amines include organic bases such as 1,8-diazabicyclo[5.4.0] undeca-7-en (DBU), 1,5-diazabicyclo[4.3.0]nonane-5-en (DBN), 6-dibutylamino1,8-diazabicyclo[5.4.0]undeca-7-en, and 1,4-diazabicyclo[2.2.2]octane (DABCO); alkali metal alkoxides such as potassium t-butoxide and sodium methoxide; and tertiary amines such as triethylamine, tri-n-butylamine, N,N-dimethylaminocyclohexylamine, and N,N,N',N'-tetramethylenediamine. DBU, DBN and DABCO are preferred. Such an isomerization assistant is usually used in an amount of approximately 0.01 to 0.3 mole, preferably approximately 0.02 to 0.2 mole, per 1 mole of the diastereomer salt.

The molar ratio of the optically active amine used as the resolving agent to the (±)-3-(3,4-dihalogenophenyl) propionic acid derivative is preferably 0.8–1.2 in view of resolving efficiency. It is also possible to prepare the optically active 3-(3,4-dihalogenophenyl)propionic acid derivatives differing in optical rotation according to the difference in optical rotation of the optically active amines. For instance, in case of using (±)-3-(3,4-dichlorophenyl)-3-methoxycarbonylpropionic acid while using 2-propanol as solvent, there can be obtained (+)-3-(3,4-dichlorophenyl)-3-methoxycarbonylpropionic acid when using (−)-1-phenylethylamine as optically active amine, and (−)-3-(3,4-dichlorophenyl)-3-methoxycarbonylpropionic acid can be obtained when using (+)-1-phenylethylamine.

The crystals of the thus obtained diastereomer salt may, if necessary, be recrystallized and then decomposed by acting a mineral acid such as hydrochloric acid or sulfuric acid, and the freed optically active 3-(3,4-dihalogenophenyl) propionic acid derivative may be extracted with an organic solvent such as ethyl acetate, ether, chloroform or toluene to obtain the objective product with high purity.

By using the thus obtained optically active products of the compounds of the formula (4), it is possible to obtain the novel naphthyridine derivatives represented by the formulae (3) and (3)'' as the optically active compounds.

The following can be cited as examples of the compounds represented by the formula (4). All of them comprehend racemates and optically active products.

3-(3,4-dichlorophenyl)-3-methoxycarbonylpropionic acid;

3-(3,4-dichlorophenyl)-3-ethoxycarbonylpropionic acid;

3-(3,4-dichlorophenyl)-3-benzyloxycarbonylpropionic acid;

3-(3,4-difluorophenyl)-3-methoxyethoxycarbonylpropionic acid.

A condensation reaction of a compound of the formula (4) with an amine compound of the formula (11) gives a compound represented by the formula (12). Such a condensation reaction can be effected by first activating a carboxylic acid of the formula (4) as an active ester, acid halide or mixed acid anhydride, and then condensing therewith an amine compound of the formula (11). For instance, the objective condensation can be accomplished by reacting a compound of the formula (4) with thionyl chloride, oxalyl chloride or the like in an aprotic solvent such as toluene, dichloroethane or tetrahydrofuan to form an acid chloride, or reacting a compound (4) with ethyl chloroformate, acetic anhydride or the like in an aprotic solvent such as mentioned above to activate the said compound as a mixed acid anhydride, and then supplying an amine compound of the formula (11) into the reaction solution.

Such condensation can also be effected by using a condensing agent such as, for example, dicyclohexylcarbodiimide, diisopropylcarbodiimide, N-3-dimethylaminopropylcarbodiimde, diphenylphosphoryl azide, propanesulfonic acid anhydride trimer (T3P) or the like. As the reaction acceletator, N-hydroxysuccinimide, 1-hydroxybenzotriazole or the like can be used. As for the reaction solvent and the reaction conditions, those commonly used for the peptide syntheses can be employed.

The amine compounds of the formula (11) can be produced by, for example, the methods described in JP-A-58-

057379, J. Heterocyclic Chem., 33, 1807 (1996), JP-A-3-2166, J. Chem. Soc., 708 (1964), J. Org. Chem, 2899 (1966), and J. Med. Chem., 32, 1295 (1989).

In the present invention, a process for producing the amine compounds of the formula (9) according to the method (xx) described above was discovered.

The compounds of the formulae (6), (7) and (8) in the method (xx) described above are mostly commercially available. For example, 2-aminobenzonitrile, N-benzylpiperidine-4-one and trimethylsilyltrifluoromethane sulfonate, which are the representative compounds of the formulae (6), (7) and (8), respectively, can be procured from Tokyo Kasei KK as reagents. Other compounds are also similarly available. Further, it is possible to produce them from a less costly material if so desired. For example, the compounds of the formula (8) wherein Y is a fluorinated alkyl sulfonate can be easily produced by the method shown in Synthesis, page 1, 1982.

Examples of the compounds represented by the formula (6) are:

2-aminobenzonitrie;

2-amino-6-methylbenzonitrile;

2-amino-6-fluorobenzonitrile;

2-amino-5-fluorobenzonitrile; and 2-amino-5-chlorobenzonitrile.

Examples of the compounds represented by the formula (7) are:

N-benzylpiperidine-4-one; and

N-methylpiperidine-4-one.

Examples of the compounds represented by the formula (8) are:

trimethylsilyltrifluoromethane sulfonate;

tert-butyldimethylsilyltrifluoromethane sulfonate;

tert-butyldiphenylsilyltrifluoromethane sulfonate;

triisopropylsilyltrifluoromethane sulfonate;

triethylsilyltrifluoromethane sulfonate;

trimethylsilylnonafluoro-n-butane sulfonate;

trimethylsilane iodide;

trimethylsilane bromide; and trimethylsilane chloride.

A process for producing an amine compound of the formula (9) is described below.

A compound of the formula (6) and a compound of the formula (7) are used in such a ratio that the amount of the compound (7) will fall within the range of 0.1 to 10 equivalents, preferably 0.7 to 3 equivalents, to one equivalent of the compound (6). The compound (6)/compound (8) ratio is such that the amount of the compound (8) will fall within the range of 0.05 to 10 equivalents, preferably 0.2 to 5 equivalents, to one equivalent of the compound (6).

As the reaction solvent, it is possible to use any type as far as it is capable of allowing the reaction to proceed, but an aprotic solvent is preferred. The aprotic solvents usable for the reaction include aromatic hydrocarbon solvents such as toluene and benzene; aliphatic hydrocarbon solvents such a hexane and pentane; ester type solvents such as ethyl acetate and methyl acetate; halogenated hydrocarbon solvents such as chloroform and methylene chloride; ether type solvents such as diethyl ether, tetrahydrofuran and diisopropyl ether; aprotic polar solvents such as dimethylformamide and dimethyl sulfoxide; and mixtures of these solvents. Of these solvents, the aromatic hydrocarbon solvents such as toluene and benzene, and ester type solvents such as ethyl acetate and methyl acetate are preferred.

The reaction can be carried out in a wide temperature range of from −78° C. to the temperature at which the solvent can be refluxed, preferably from room temperature to the solvent-refluxed temperature. The reaction time is not specifically defined; the reaction is allowed to continue until it is completed. The reaction product obtained according to the process of the present invention may be filtered or extracted with water to provide it as a salt, for example, as a sulfonate, iodide or bromide. Further, a base may be acted to the obtained salt to render it into a free form, the latter being subjected to an ordinary purification means such as extraction with an organic solvent, chromatography, distillation, crystallization, suspension purification, etc., to obtain an amine compound of the formula (9).

The compounds of the formula (9), where $R_5$ is a benzyl group, can be easily led into the corresponding amine compounds of the formula (11) by a hydrogenation reducing reaction. As the catalyst for this reaction, palladium or platinum type catalysts can be used. As the solvent, alcohol or ether type solvents, water, acetic acid, trifluoroacetic acid and the like can be used. The reaction is carried out at a temperature of from −20° C. to 200° C., under a pressure of from normal pressure to 100 atm for a period of from 5 minutes to 48 hours. As the hydrogen source, hydrogen gas, 1,4-cyclohexadiene, formic acid and the like can be used.

Examples of the amine compounds represented by the formula (11) are:

1,2,3,4,6,7,8,9-octahydro-benzo[b][1,6]-naphthyridine;

10-chloro-1,2,3,4-tetrahydro-benzo[b][1,6]-naphthyridine;

10-amino-1,2,3,4-tetrahydro-benzo[b][1,6]-naphthyridine; and 10-phenyl-1,2,3,4-tetrahydro-benzo[b][1,6]-naphthyridine.

Further, by hydrolyzing the compounds of the formula (12) in a solvent, for example, an alcohol such as methanol or ethanol, an ether such a tetrahydrofuran or 1,4-dioxane, water, or a mixture thereof, in the presence of a basic catalyst such as sodium hydroxide or potassium carbonate or an acid catalyst such as p-toluenesulfonic acid, there can be obtained the compounds represented by the formula (13).

When $R_4$ in the compounds of the formula (12) is a benzyl group, it is possible to obtain the compounds of the formula (13) by subjecting the compounds (12) to a hydrogenation reduction reaction using a palladium type or platinum type catalyst. As the solvent, the alcohol type or ether type, water, etc., can be used. The reaction is carried out at a temperature of from −20° C. to 100° C. for a period of from 5 minutes to 48 hours. As the hydrogen source, hydrogen gas, 1,4-cyclohexadiene, formic acid and the like can be used.

By reacting the compounds of the formula (13) with thionyl chloride, oxalyl chloride or the like in an aprotic solvent such as toluene, dichloromethane or tetrahydrofuran to form an acid chloride, or reacting the said compounds with chloroethyl formate, acetic anhydride or the like in an aprotic solvent such as mentioned above to form a mixed acid anhydride, activating this reaction product and further subjecting it to a condensation reaction with methylamine, the compounds of the formula (14) can be obtained.

Condensation can be effected by using a condensing agent. As the condensing agent, dicyclohexylcarbodiimide, diisopropylcarbodiimide, N-3-dimethylaminopropylcarbodiimide, diphenylphosphorylazide, propanesulfonic anhydride trimer (T3P) and the like can be used. As the reaction accelerator, N-hydroxysuccinimide, 1-hydroxybenzotriazole and the like can be used. The reaction solvent and the reaction conditions may be the same as those used for the ordinary peptide syntheses.

The compounds of the formula (14) can be transformed into the compounds of the formula (1) by subjecting the compounds (14) to a reduction reaction under the range of −20° C. to solvent-reflux temperature, using a strong reducing agent such as diborane or alkylborane including dimethylborane sulfide, lithium aluminum hydride, diisobutyl aluminum hydride or aluminum hydride in an aprotic solvent such as dichloromethane, tetrahydrofuran or diethyl ether. Diborane or a borane-ligand complex is preferably used. For example, the objective reductants, or the compounds of the formula (1), can be obtained by a method using a borane-tetrahydrofuran complex which is available from Aldrich, etc., or a method in which sodium boron hydride and a boron trifluoride-ether complex are acted to produce diborane or a borane-ligand complex in the reactor.

Examples of the compounds represented by the formula (1) are shown below. All of these compounds include the racemates and the optically active version.

2-[4-(N-methyl)amino-3-(3,4-dichlorophenyl)butyl]-1,2,3,4,6,7,8,9-octahydro-benzo[b][1,6]-naphthyridine;

10-amino-2-[4-(N-methyl)amino-3-( 3,4-difluorophenyl)butyl]-1,2,3,4,6,7,8,9-octahydrobenzo[b][1,6]-naphthyridine;

2-[4-(N-methyl)amino-3-(3,4-dichlorophenyl)butyl]-10-phenyl-1,2,3,4-tetrahydrobenzo[b][1,6]-naphthyridine;

10-amino-2-[4-(N-methyl)amino-3-(3,4-dichlorophenyl)butyl]-7-trifluoromethyl-1,2,3,4-tetrahydrobenzo[b][1,6]-naphthyridine.

The compounds of the formula (1) can be converted into the novel naphthyridine derivatives of the formula (3) by subjecting the compounds (1) to a condensation reaction with a carboxylic acid of the formula (2) or a derivative thereof. Condensation can be effected by a method using a commercially available acylating agent as the carboxylic acid derivative of the formula (2). As the acylating agent, acid anhydrides such as benzoic anhydride, acid halides such as benzoyl chloride and p-anisoyl chloride, diketenes and the like can be used. Acid anhydrides or acid chlorides are preferred.

It is also possible to employ a process in which a carboxylic acid of the formula (2) is activated as an active ester, acid halide or mixed acid anhydride, and successively a compound of the formula (1) is condensed therewith. In this case, for instance, the following methods can be used: the compound (1) is reacted with thionyl chloride or oxalyl chloride in an aprotic solvent such as toluene, dichloromethane or tetrahydrofuran to form an acid halide; the compound (1) is reacted with chloroethyl formate, acetic anhydride or the like in an aprotic solvent such as mentioned above to form a mixed acid anhydride and this product is activated; or the compound (1) is reacted with 1,1'-carbonyldiimidazole or the like in an aprotic solvent such as mentioned above and thereby activated.

It is also possible to carry out the condensation reaction of a compound of the formula (1) with a carboxylic acid of the formula (2) by using a condensing agent. As the condensing agent, dicyclohexylcarbodiimide, diisopropylcarbodiimide, N-3-dimethylaminopropylcarbodiimde, diphenylphosphoryl azide, propanesulfonic anhydride trimer (T3P) and the like can be used. As the reaction accelerator, N-hydroxysuccinimide, 1-hydroxybenzotriazole and the like can be used.

As the reaction solvent, there can be used halogen type solvents such as dichloromethane and chloroform, aprotic polar solvents such as dimethylformamide and 1,3-dimethyl-2-imidazolidinone, ethers such as tetrahydrofuran and dioxane, water, and mixtures thereof.

The reaction can be conducted in a temperature range of from −78° C. to around the boiling point of the solvent used, preferably from −30° C. to 50° C., more practically from −20° C. to 40° C.

As shown in Scheme 2, the novel naphthyridine derivatives represented by the formula (3)", which are part of the novel naphthyridine derivatives of the present invention, can be obtained by acylating the amino group of the novel naphthyridine derivatives represented by the formula (3)'.

As the acylating agent, acid anhydrides such as acetic anhydride and propionic anhydride, acid halides such as benzoyl chloride and p-anisoyl chloride, diketene, and the like can be used, but acid anhydrides are preferred. If necessary, an acid catalyst may be introduced. As the acid, hydrochloric acid, sulfuric acid, phosphoric acid and the like can be used, with phophoric acid being preferred.

A reaction solvent may or may not be used. The solvents usable for the reaction include halogen type solvents such as dichloromethane and chloroform; aprotic polar solvents such as dimethylformamide, diglyme (diethylene glycol dimethyl ether) and 1-methyl-2-pyrrolidinone; ethers such as tetrahydrofuran and dioxane; basic solvents such as triethylamine and pyridine; and mixtures of these solvents. Aprotic polar solvents such as 1-methyl-2-pyrrolidinone or basic solvents such as triethylamine and pyridine are preferably used.

The reaction can be carried out in a temperature range of from −40° C. to around the boiling point of the solvent used, preferably from 0° C. to around the boiling point of the solvent, more preferably from 60° C. to 130° C.

The novel naphthyridine derivatives of the present invention represented by the formulae (3) and (3)" can be produced according to a conventional synthesis process shown as Scheme 3 below.

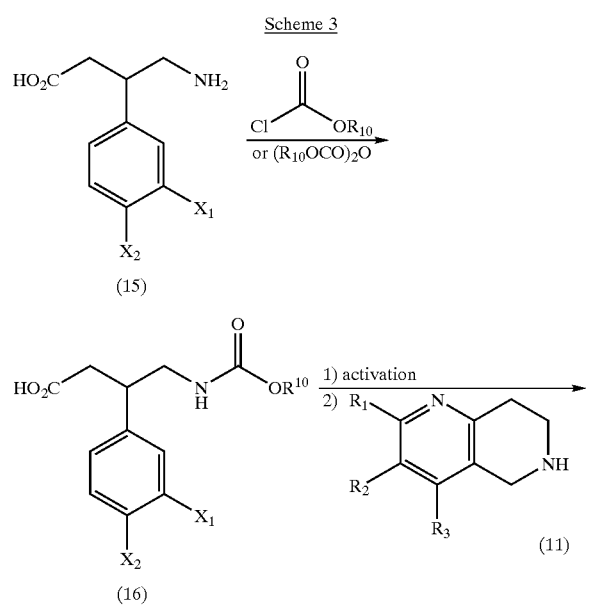

$R_{10}$: lower alkyl group

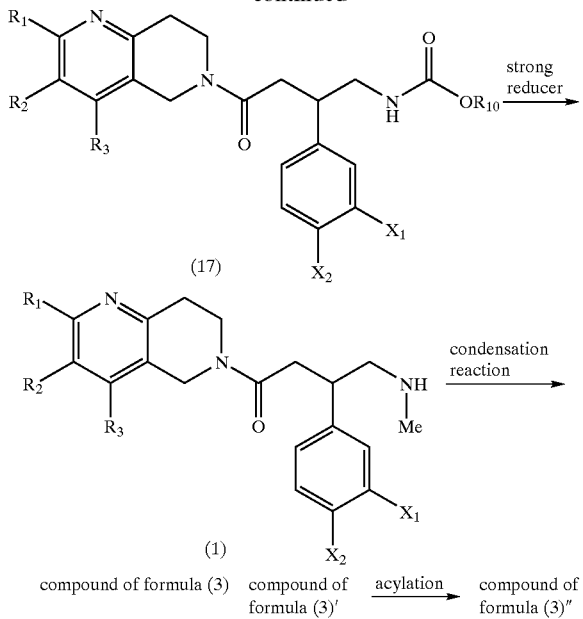

compound of formula (3)    compound of formula (3)'   —acylation→   compound of formula (3)"

In Scheme 3, 4-amino-3-(3,4-dihalogeno-substituted phenyl)butyric acid of the formula (15) used as the starting material can be produced by, for example, the method described in Acta Pharmaceutical Sinica 1990; 25(1) : 11–17.

An optically active compound of the formula (15) can be obtained by, for example, the method disclosed in JP-A-3-206086, so that by using such an optically active compound as the starting material, it is possible to obtain a novel naphthyridine derivative of the present invention represented by the formula (3) or (3)" as an optically active compound.

The compound of the formula (15) is subjected to a condensation reaction with an acid chloride such as chloroethyl formate or an acid anhydride such as di-tert-butyl-dicarbonate in a solvent such as dichloromethane, tetrahydrofuran, 1,4-dioxane, water or a mixture thereof to provide a compound represented by the formula (16).

This compound of the formula (16) is further reacted with thionyl chloride, oxalyl chloride or the like in an aprotic solvent such as toluene, dichloromethane or tetrahydrofuran to form an acid chloride, or reacted with chloroethyl formate, acetic anhydride or the like in an aprotic solvent such as mentioned above to form a mixed acid anhydride, and this product is activated and subjected to a condensation reaction with an amine compound of the formula (11) to give a compound of the formula (17).

This formula (17) compound can be turned into a compound of the formula (1) by subjecting the formula (17) compound to a reduction reaction under reflux at a temperature of from −20° C. to a heating temperature in an aprotic solvent such as dichloromethane, tetrahydrofuran or diethyl ether by using a strong reducing agent such as diborane containing dimethylborane sulfide, lithium aluminum hydride or diisobutyl aluminum hydride.

Following thereafter the same procedure as described above, it is possible to produce a novel naphthyridine derivative of the present invention represented by the formula (3) or (3)".

In use of the novel naphthyridine derivatives of the present invention represented by the formulae (3) and (3)" as a tachykinin receptor antagonist, they are worked into various forms of preparation such as suspension, emulsion, injection, inhalant, tablet, pill, granule, powder, capsule, peroral liquid, supposition, eye drops, eye ointment, percutaneous liquid, ointment, permucous attachment, spray, etc., either independently or after being mixed with an appropriate excipient or carrier, and administered perorally or parenterally.

The adjuvants used as excipient or carrier are the pharmacologically acceptable ones, and their type and composition are decided depending on the course and way of administration. For instance, in the case of injections, starch, lactose, crystal cellulose, magnesium stearate or the like is preferably selected as adjuvant. Other ordinarily used adjuvants such as auxiliary agent, stabilizer, wetting agent, emulsifier, buffer, etc., may be contained as desired in the above preparations.

The content of the novel naphthyridine derivative in the preparations, though variable depending on the type of the preparation, is usually 0.1 to 100% by weight, preferably 1 to 98% by weight. For example, in the case of injection, it is prepared so that a novel naphthyridine derivative will be contained in an amount of usually 0.1 to 30% by weight, preferably 1 to 10% by weight. In the case of peroral preparations, they are used in the form of tablet, capsule, powder, granule, liquid, dry syrup or the like with the adjuvants. Such a tablet, capsule, powder and granule contains usually 5 to 100% by weight, preferably 25 to 98% by weight of a novel naphthyridine derivative.

Dosage is decided by taking into consideration the patient's age, sex, body weight, condition, therapeutical purpose and other factors, but it is usually 0.001 to 100 mg/kg/day for parenteral administration and 0.01 to 500 mg/kg/day for peroral administration, and this dosage may be given either all at one time or in two to four portions.

The present invention is further illustrated by the following examples, but the scope of the present invention is not limited by these examples in any way. The NMR values given in the Examples are the values (δ,ppm) determined by using a 60 or 200 MHz nuclear magnetic resonance system with tetramethylsilane as an internal standard.

EXAMPLE 1

Synthesis of (±)-10-Amino-2-[4-(N-benzoyl-N-methyl)-amino-3-(3,4-dichlorophenyl)butyl]-1,2,3,4,6,7,8,9-octahydrobenzo[b][1,6]-naphthyridine To a dichloromethane (5 ml) solution of (±)-10-amino-2-[4-(N-methyl)amino-3-(3,4-dichlorophenyl)butyl]-1,2,3,4,6,7,8,9-octahydro-benzo[b][1,6]-naphthyridine (997 mg, 2.3 mol), benzoyl chloride (0.267 ml, 2.3 mmol) was added under cooling with ice water and stirred for 20 minutes. An aqueous solution of saturated sodium hydrogencarbonate was added to the reaction solution, and the mixed solution was extracted with dichloromethane. After drying over anhydrous sodium sulfate, the organic layer was concentrated under reduced pressure to give the objective title compound (1,228 g, 99% yield) as a light yellow amorphous substance.

$^1$H-NMR (200 MHzFT, TMS, CDCl$_3$), 1.60–4.00 (26H, complex), 6.70–7.60 (8H, complex). MS (FAB, m-NBA); m/z-→537, 539 [M+H]+.

EXAMPLE 2

Synthesis of (±)-2-[4-(N-Benzoyl-N-methyl)amino-3-(3,4-dichlorophenyl)butyl]-1,2,3,4,6,7,8,9-octahydro-benzo[b][1,6]-naphthyridine The title compound was obtained in the same way as in Example 1.

$^1$H-NMR (200 MHzFT, TMS, CDCl$_3$), 1.70–1.98 (4H, m), 2.10–4.00 (20H, complex), 6.70–7.50 (9H, complex). MS (FAB, m-NBA); m/z→522, 524 [M+H]+.

EXAMPLE 3

Synthesis of (±)-10-Acetylamino-2-[4-(N-benzoyl-N-methyl)amino-3-(3,4-dichlorophenyl)butyl]-1,2,3,4,6,7,8,9-octahydrobenzo[b][1,6]-naphthyridine (±)-10-amino-2-[4-(N-benzoyl-N-methyl)amino-3-(3,4-dichlorophenyl)butyl]-1,2,3,4,6,7,8,9-octahydrobenzo[b][1,6]-naphthyridine (150 mg, 0.28 mmol) was dissolved in pyridine (0.113 ml, 1.4 mmol), to which acetic anhydride (53 μl) was added and the solution was stirred overnight at 80° C. To the reaction solution were added pyridine (0.5 ml) and acetic anhydride (0.3 ml). After further stirring for 8 hours, the reaction solution was concentrated under reduced pressure and the residue was purified by silica gel column chromatography (dichloromethane/methanol=20/1) to give a yellow amorphous substance (46 mg). 2N sodium hydroxide (0.1 ml) was added thereto and the solution was stirred at room temperature for 2 hours. Water and a saturated saline solution were added to the reaction solution, and the mixed solution was extracted with dichloromethane. The obtained organic layer was dried over anhydrous sodium sulfate and concentrated under reduced pressure to obtain the objective title compound (35 mg, 22%) as a light yellow amorphous substance.

$^1$H-NMR (200 MHzFT, TMS, CD$_3$OD), 1.70–1.95 (4H, complex), 2.16 (3H, s), 2.50–3.90 (20H, complex), 6.87–7.68 (8H, m). MS (FAB, m-NBA); m/z→579, 581 [M+H]+.

EXAMPLE 4

Synthesis of (±)-10-Acetylamino-2-[4-(N-benzoyl-N-methyl)amino-3-(3,4-dichlorophenyl)butyl]-1,2,3,4,6,7,8,9-octahydrobenzo[b][1,6]-naphthyridine (±)-10-amino-2-[4-(N-benzoyl-N-methyl)amino-3-(3,4-dichlorophenyl)butyl]-1,2,3,4,6,7,8,9-octahydrobenzo[b][1,6]-naphthyridine (43 g, 0.08 mol) was dissolved with NMP (40 ml), to which acetic anhydride (226.48 ml, 2.40 mol) was added dropwise at an internal temperature of 20 to 30° C. in a stream of nitrogen over a period of 10 minutes. Phosphoric acid (54.74 ml, 0.80 mol) was further added dropwise over a period of 10 minutes while maintaining the internal temperature at 50° C. or below. Then the internal temperature was raised to about 95 to 105° C. and the solution was stirred for about 10 hours. The internal temperature of the reaction solution was then lowered to around 10 to 20° C., and the reaction solution was added dropwise to 5° C. methanol (80 ml) and ethyl acetate (400 ml) for 30 minutes while maintaining the internal temperature at 5 to 25° C., and the mixture was further stirred for 1 to 2 hours with the internal temperature kept at 15 to 25° C. Thereafter, the suspension was cooled to an internal temperature of about 5 to 10° C., and a 4N sodium hydroxide solution (1,200 ml, 4.80 mol) was added dropwise over a period of 1.5 hour while maintaining the internal temperature at 25° C. or below. Ethyl acetate (400 ml) was added thereto, and after liquid separation, the organic layer was washed with a 10% saline solution (400 ml) and then concentrated under reduced pressure to give the objective title compound (46.4 g, 100%).

EXAMPLE 5

Synthesis of 3,4-Dichlorophenylacetate 90.05 g of 3,4-dichlorophenylacetic acid was dissolved in 120 ml of methanol, to which 2.0 ml of 95% sulfuric acid was added and the solution was stirred at 60° C. for approximately 9 hours. After further stirring overnight at room temperature, 300 ml of a saturated sodium hydrogencarbonate solution and 100 ml of ethyl acetate were added, followed by vigorous stirring of the solution, and the organic layer was separated. The aqueous layer was extracted once each with 300 ml and 200 ml of ethyl acetate, then joined with the organic layer and washed with 200 ml of water and 200 ml of a saturated saline solution. The organic layer was dried over 80 g of anhydrous sodium sulfate and the solvent was distilled away to give a slightly yellow oily substance. This oily substance was distilled under reduced pressure to obtain 99.00 g (94.0% yield) of the title substance.

$^1$H-NMR (60 MHz, TMS, CDCl$_3$); 3.52 (2H, s), 3.63 (3H, s), 7.04 (1H, dd, J=2.0, 8.0 Hz), 7.30 (1H, d, J=2.0 Hz), 7.32 (1H, d, J=8.0 Hz). b.p. 125–127° C./5 mmHg.

EXAMPLE 6

Synthesis of 3-(3,4-Dichlorophenyl)-3-methoxycarbonyl propionic Acid 17.94 g of sodium hydride with 61% purity and 350 ml of dried dimethyl sulfoxide were added to a well dried 1-litre 4-necked flask and suspended at room temperature. 99.00 g of methyl 3,4-dichlorophenylacetate was added dropwise thereto under cooling with ice water, the solution being continuously stirred at room temperature even after the end of the dropwise addition. Then 50.38 g of sodium chloroacetate was added under cooling with ice water and the solution was stirred at room temperature. The produced red suspension was poured into a mixture of 500 ml of 1N hydrochloric acid and 300 ml of ice water, and the solution was stirred vigorously. The reaction mixture was extracted with 800 ml of ether, and the organic layer was washed with 500 ml of water (three times) and 500 ml of a saturated saline solution (once). The organic layer was dried over anhydrous sodium sulfate and the solvent was distilled away to obtain 123.94 g of an oily substance. This oily substance was crystallized by treating it with about 400 ml of an ethyl acetate/hexane (1/20) mixture. The precipitated crystals were filtered out, washed with a small quantity of ethyl acetate/hexane (1/20) and then dried to give 93.46 g of the primary crystals of the title substance. Meanwhile, the filtrate was concentrated and crystallized from ethyl acetate/hexane, and the precipitated crystals were filtered out and dried to obtain 9.29 g of the secondary crystals (102.75 g with the primary and secondary crystals put together, 81.0% yield) of the title substance.

$^1$H-NMR (200 MHzFT, TMS, CDCl$_3$); 2.71 (1H, dd, J=5.7, 17.4 Hz), 3.23 (1H, dd, J=9.6, 17.4 Hz), 3.70 (3H, s), 4.02 (1H, dd, J=5.7, 9.6 Hz), 7.13 (1H, dd, J=2.2, 8.4 Hz), 7.39 (1H, d, J=2.2 Hz), 7.41 (1H, d, J=8.4 Hz), MS(FAB, m-NBA); m/z-→277 [M+H]+.

EXAMPLE 7

Synthesis of Ethyl 3,4-Dichlorophenylacetate 90.05 g of 3,4-dichlorophenylacetic acid was dissolved in 150 ml of ethanol, and the solution was treated according to the procedure of Example 5 to obtain 101.30 g (90.0% yield) of the title substance.

$^1$H-NMR (600 MHz, TMS, CDCl$_3$); 1.24 (3H, t, J=6.0 Hz), 3.52 (2H, s), 4.08 (2H, q, J=6.0 Hz), 7.10 (1H, dd, J=2.0, 8.0 Hz), 7.32 (1H, d, J=8.0 Hz), 7.33 (1H, d, J=2.0 Hz), b. p. 136–138° C./7 mmHg.

EXAMPLE 8

Synthesis of 3-(3,4-Dichlorophenyl)-3-ethoxycarbonylpropionic Acid 16.50 g of sodium hydride with 64% purity and 350 ml of dry dimethyl sulfoxide were supplied to a well dried 1-litre 4-necked flask. Then 101.30 g of ethyl 3,4-dichlorophenylacetate obtained in Example 6 was added dropwise, the solution being stirred at room temperature even after the end of the dropwise addition. Thereafter, 48.61 g of sodium chloroacetate was added and the solution was further stirred at room temperature. At this point, the reaction solution changed from a yellow to a red suspension. The reaction solution was stirred overnight at room temperature, then poured into a mixture of 500 ml of 1N hydrochloric acid and 300 ml of ice water, and stirred vigorously. The reaction mixture was extracted with 800 ml of ether and the organic layer was washed with 500 ml of water (three times) and 500 ml of a saturated saline solution (once). This organic layer was then dried over approximately 50 g of anhydrous sodium sulfate, concentrated to approximately 50 ml solvent and crystallized by treating it with approximately 300 ml of an ether/hexane mixed solvent. The precipitated crystals were filtered out and dried to give 106.07 g of primary crystals of the title substance. Meanwhile, the filtrate was concentrated to produce an oily substance, and it was crystallized by adding 20 ml of ether and 60 ml of hexane. Further, after additional supply of hexane, the precipitated crystals were filtered out and dried to obtain 3.09 g of the secondary crystals (109.16 g when combined with the primary crystals, yield 84.0%) of the title substance.

$^1$H-NMR (200 MHzFT, TMS, CDCl$_3$); 1.21 (3H, t, J=7.2 Hz), 2.70 (1H, dd, J=5.7, 17.4 Hz), 3.21 (1H, dd, J=9.6, 17.4 Hz), 4.00 (1H, dd, J=5.7, 9.6 Hz), 4.15 (2H, q, J=7.0 Hz), 7.13 (1H, dd, J=2.1, 8.4 Hz), 7.39 (1H, s), 7.41 (1H, d, J=8.4 Hz). MS(FAB, m-NBA); m/z-→291 [M+H]+.

EXAMPLE 9

Synthesis of Benzyl 3,4-Dichlorophenyl Acetate 41.01 g (0.200 mol) of dichlorophenylacetic acid and 22.71 g (0.210 mol) of benzyl alcohol were dissolved in 200 ml of toluene, to which 0.38 g (0.002 mol) of p-toluenesulfonic acid monohydrate was added and the mixture was stirred under reflux for 7 hours. The internal temperature was lowered to 30° C. and 200 ml of a 2% sodium hydrogencarbonate solution was added. After separating the liquid, the organic layer was washed with 200 ml of water and concentrated under reduced pressure to give 59.39 g (100% yield) of benzyl 3,4-dichlorophenylacetate.

$^1$H-NMR (200 MHzFT, TMS, CDCl$_3$); 3.62 (2H, s), 5.14 (2H, s), 7.12 (1H, dd, J=2.0, 8.3 Hz), 7.23–7.41 (7H, m). b. p.; 183~184° C./3.5 mmHg.

EXAMPLE 10

Synthesis of 3-(3,4-Dichlorophenyl)-3-benzyloxycarbonylpropionic Acid

To a DMSO (50 ml) suspension of 3.63 g (0.100 mol) of sodium hydride, a DMSO solution (30 ml) of 31.57 g (0.100 mol) of benzyl 3,4-dichlorophenylacetate was added at a temperature of 30° C. or below over a period of 45 minutes, and then the solution was further stirred at an internal temperature of 25° C. for 45 minutes. Then 11.65 g (0.100 mol) of sodium chloroacetate was added over a period of 10 minutes and the suspension was stirred at an internal temperature of 25° C. for 18.5 hours. The reaction solution was added dropwise into 50 ml of 2N hydrochloric acid and 250 ml of ice water while maintaining the internal temperature at 20° C. or below, and then 250 ml of ethyl acetate was added to the mixed solution. After separating the liquid, the organic layer was washed with 250 ml of water and then further washed with 250 ml of a 5% saline solution. It was then concentrated under reduced pressure, again concentrated under reduced pressure by adding 50 ml of toluene and further concentrated under reduced pressure by additionally adding 50 ml of toluene to obtain a crude product. Then 100 ml of toluene was added and the solution was heated to an internal temperature of 90° C. and stirred for one hour, after which 100 ml of heptane was added at an internal temperature of 80° C. and the solution was cooled slowly until the internal temperature dropped to 25° C. The precipitated crystals were filtered out and washed twice with 25 ml of heptane to obtain 26.40 g (74.7% yield) of the title compound.

$^1$H-NMR (200 MHzFT, TMS, CDCl$_3$); 2.73 (1H, dd, J=5.7, 17.4 Hz), 3.25 (1H, dd, J=9.5, 17.4 Hz), 4.07 (1H, dd, J=5.7, 9.5 Hz), 5.13 (2H, dd, J=12.3, 17.8 Hz), 7.10 (1H, dd, J=2.2, 8.4 Hz), 7.19~7.41 (8H, m). MS (FAB, m-NBA); m/z-→353, 355 [M+H]+.

EXAMPLE 11

Synthesis of Optically Active 3-(3,4-Dichlorophenyl)-3-methoxycarbonylpropionic Acid·(S)-1-phenylethylamine Salt 1.21 g (10.0 mmol) of (−)-1-phenylethylamine and 20 ml of ethanol were added to 2.77 g (10.0 mmol) of (±)-3-(3,4-dichlorophenyl)-3-methoxycarbonylpropionic acid, and the mixture was stirred in a suspended state under heating at a bath temperature of 90 to 110° C. for 4 hours. Then the internal temperature was lowered to 20° C. and the suspension was stirred at this temperature for one hour. The precipitated crystals were filtered out, washed with a small quantity of ethanol and dried to harvest 2.70 g (68.0% yield) of (+)-3-(3,4-dichlorophenyl)-3-methoxycarbonylpropionic acid·(S)-1-phenylethylamine salt.

$^1$H-NMR (200 MHzFT, TMS, CD$_3$OD); 1.60 (3H, d, J=6.9 Hz), 2.51 (1H, dd, J=6.3, 16.0 Hz), 2.95 (1H, dd, J=9.2, 16.0 Hz), 3.65 (3H, s), 4.06 (1H, dd, J=6.3, 9.2 Hz), 4.40 (1H, q, J=6.9 Hz), 7.23 (1H, dd, J=2.1, 8.3 Hz), 7.30–7.51 (7H, m).

Part of this salt was methyl-esterified by adding trimethylsilyldiazomethane at room temperature to obtain dimethyl 2-(3,4-dichlorophenyl)succinate. HPLC analysis using an optically active column (CHIRACEL OD, Dicel Chemical Industries Co., Ltd.) confirmed that this product had an optical purity (e.e.) of 62.8%.

On the other hand, the salt recovered by removing the solvent from the filtrate and washings containing (−)-3-(3,4-dichlorophenyl)propionic acid·(S)-1-phenylethylamine salt had an optical purity (e.e.) of 66.6%.

EXAMPLE 12

Synthesis of Optically Active 3-(3,4-Dichlorophenyl)-3-methoxycarbonylpropionic Acid·(S)-1-phenylethylamine Salt 1.21 g (10.0 mmol) of (−)-1-phenylethylamine and 25 ml of 1-propanol were added to 2.77 g (10.0 mmol) of (±)-3-(3,4-dichlorophenyl)-3-methoxycarbonylpropionic acid and dissolved by heating. Then the solution was cooled to an internal temperature of 90° C. and inoculated with the separately prepared seed crystals. The solution was then cooled to an internal temperature of 70 to 72° C. and stirred in a suspended state for 8 hours. Then the solution was further cooled to an internal temperature of 20° C. and stirred at this temperature for 0.5 hour, and the precipitated crystals were filtered out, washed with a small quantity of 1-propanol and dried to obtain 2.13 g (53.6% yield) of (+)-3-(3,4-dichlorophenyl)-3-methoxycarbonylpropionic acid·(S)-1-phenylethylamine salt.

Part of this salt was methyl-esterified by adding trimethylsilyldiazomethane at room temperature to obtain dimethyl 2-(3,4-dichlorophenyl)succinate. This compound was determined to have an optical purity (e.e.) of 81.1% by HPLC analysis using an optically active column (CHIRACEL OD, Dicel Chemical Industries Co., Ltd.).

On the other hand, the salt recovered by removing the solvent from the filtrate and washings containing (−)-3-(3, 4-dichlorophenyl)propionic acid·(S)-1-phenylethylamine salt was found to have an optical purity (e.e.) of 63.6%.

EXAMPLE 13

Synthesis of (+)-3-(3,4-Dichlorophenyl)-3-methoxycarbonylpropionic Acid·(S)-1-phenylethylamine Salt 1.22 g (10.1 mmol) of (−)-1-phenylethylamine, 0.0766 g (0.503 mmol) of 1,8-diazobicyclo[5.4.0]-undeca-7-ene (hereinafter abbreviated as DBU) and 23.9 ml of 2-propanol were added to 2.77 g (10.0 mmol) of (±)-3-(3,4-dichlorophenyl)-3-methoxycarbonylpropionic acid and heated until the internal temperature became 72° C. With this temperature maintained, the solution was stirred in a suspended state for 8 hours, then it was cooled to an internal temperature of 20° C. and further stirred at this temperature for 0.5 hour. The precipitated crystals were filtered out, washed with a small amount of 2-propanol and dried to obtain 3.37 g (84.7% yield) of (+)-3-(3,4-dichlorophenyl)-3-methoxycarbonylpropionic acid·(S)-1-phenylethylamine salt.

Part of this salt was methyl-esterified by adding trimethylsilyldiazomethane at room temperature to obtain dimethyl 2-(3,4-dichlorophenyl)succinate. HPLC analysis using an optically active column (CHIRALCEL OD, Dicel Chemical Industries Co., Ltd.) showed that this substance had an optical purity (e.e.) of 96.9%.

On the other hand, the salt recovered by removing the solvent from the filtrate and washings containing (−)-3-(3, 4-dichlorophenyl)-3-methoxycarbonylpropionic acid·(S)-1-phenylethylamine salt had an optical purity (e.e.) of 70.9%.

EXAMPLES 14 TO 22

The procedure of Example 12 or 13 was carried out on the scale of 10 mmol by changing the reaction conditions. The reaction conditions, yield of (+)-3-(3,4-dichlorophenyl)-3-methoxycarbonylpropionic acid·(S)-1-phenylethylamine salt, and optical purity of (+)-3-(3,4-dichlorophenyl)-3-methoxycarbonylpropionic acid are shown collectively in Table 1.

TABLE 1

| Example | Solvent (amount per 1g of salt) [ml] | Temperature [° C.] | Time [h] | DB [equivalents] | Yield [%] | Optical purity [% e.e.] |
|---|---|---|---|---|---|---|
| 14 | 1-propanol (6.3) | 72 | (36) | | 61.0 | 96.0 |
| 15 | 1-propanol (6.3) | 72 | (8) | 0.1 | 68.7 | 86.0 |
| 16 | 1-propanol (6.3) | 72 | (24) | 0.1 | 66.8 | 88.7 |
| 17 | 1-propanol (3.5) | 72 | (8) | 0.1 | 78.7 | 94.5 |
| 18 | 1-propanol (2.5) | 72 | (8) | 0.1 | 82.3 | 95.3 |
| 19 | 2-propanol (6.3) | 72 | (8) | 0.1 | 84.6 | 97.5 |
| 20 | 2-propanol (6.3) | 72 | (8) | 0.026 | 83.4 | 84.2 |
| 21 | 2-propanol (6.0) | 80 | (8) | 0.026 | 83.2 | 87.0 |
| 22 | 2-propanol (3.5) | 80 | (8) | 0.025 | 87.9 | 90.1 |

EXAMPLE 23

Optical Purification of Optically Active 3-(3,4-Dichlorophenyl)-3-methoxycarbonylpropionic Acid·(S)-1-phenylethylamine Salt The (+)-3-(3,4-dichlorophenyl)-3-methoxycarbonylpropionic acid·(S)-1-phenylethylamine salts obtained in Examples 12, 15, 16, 20, 21 and 22 were put together to provide a salt with an optical purity of 86.5% e.e. To 17.60 g of this salt, 52.8 ml of 2-propanol was added and the solution was heated to an internal temperature of 72 to 74° C. With this temperature maintained, the solution was stirred in a suspended state for 30 minutes, then cooled to an internal temperature of 20° C. and stirred at this temperature for 20 minutes. The precipitated crystals were filtered out, washed thrice with 5 ml of 2-propanol and then dried to produce 16.73 g (95.0% yield) of (+)-3-(3,4-dichloropheny)-3-methoxycarbonylpropionic acid·(S)-1-phenylethylamine salt.

Part of this salt was methyl-esterified by adding trimethylsilyldiazomethane at room temperature to obtain dimethyl 2-(3,4-dichlorophenyl)succinate. HPLC analysis using an optically active column (CHIRALCEL OD, Dicel Chemical Industries Co., Ltd.) showed that this substance had an optical purity (e.e.) of 98.1%.

EXAMPLE 24

Optical Purification of Optically Active 3-(3,4-Dichlorophenyl)-3-methoxycarbonylpropionic Acid·(S)-1-phenylethylamine Salt To 17.40 g of (+)-3-(3,4-dichlorophenyl)-3-methoxycarbonylpropionic acid·(S)-1-phenylethylamine salt with an optical purity of 86.5% e.e., obtained in the same way as in Example 15, 104.4 ml of 2-propanol was added and the solution was heated to an internal temperature of 70° C. With this temperature maintained, the solution was stirred in a suspended state for 30 minutes, then cooled to an internal temperature of 20° C. and stirred at this temperature for 30 minutes. The precipitated crystals were filtered out, washed twice with 10 ml of 2-propanol and dried to obtain 16.39 g (94.2% yield) of (+)-3-(3,4-dichlorophenyl)-3-methoxycarbonylpropionic acid·(S)-1-phenylethylamine salt.

$[\alpha]_D^{20}$ +59.9°, $[\alpha]_{436}^{20}$+128.6° (c=1.00, methanol).

Part of this salt was methyl-esterified by adding trimethylsilyldiazomethane at room temperature to obtain dimethyl 2-(3,4-dichlorophenyl)succinate and it was subjected to HPLC analysis using an optically active column (CHIRALCEL OD, Dicel Chemical Industries Co., Ltd.), which showed that this substance had an optical purity (e.e.) of 97.4%.

EXAMPLE 25

Optical Purification of Optically Active 3-(3,4-Dichlorophenyl)-3-methoxycarbonylpropionic Acid·(S)-1-phenylethylamine Salt To 2.66 g of (+)-3-(3,4-dichlorophenyl)-3-methoxycarbonylpropionic acid·(S)-1-phenylethylamine salt with an optical purity (e.e.) of 62.8%, obtained in the same way as in Example 11, 8 ml of ethanol was added and the solution was heated to an internal temperature of 60 to 64° C. With this temperature maintained, the solution was stirred in a suspended state for 30 minutes, then cooled to an internal temperature of 20° C. and stirred at the same temperature for 30 minutes. The precipitated crystals were filtered out, washed with a small quantity of ethanol and dried to obtain 2.24 g (85.9% yield) of (+)-3-(3,4-dichlorophenyl)-3-methoxycarbonylpropionic acid·(S)-1-phenylethylamine salt.

Part of this salt was methyl-esterified by adding trimethylsilyldiazomethane at room temperature to obtain dimethyl 2-(3,4-dichlorophenyl)succinate. HPLC analysis using an optically active column (CHIRALCEL OD, Dicel Chemical Industries Co., Ltd.) showed that this substance had an optical purity (e.e.) of 97.1%.

EXAMPLE 26

Preparation of Optically Active 3-(3,4-Dichlorophenyl)-3-methoxycarbonylpropionic Acid 4.00 g (10.0 mmol) of (+)-3-(3,4-dichlorophenyl)-3-methoxycarbonylpropionic acid·(S)-1-phenylethylamine salt obtained in Example 24 was suspended in 12.0 ml of ethyl acetate and cooled with ice water. 12.1 ml of 1N hydrochloric acid was added thereto to decompose the salt and the organic layer was separated. The aqueous layer was extracted twice with 6.0 ml of ethyl acetate, then joined with the previously separated organic layer and washed with 10 ml each of 1N hydrochloric acid, water and a saturated saline solution (twice). The organic layer was dried over anhydrous sodium sulfate and the solvent was distilled away to obtain 2.77 g (99.4% yield) of (+)- 3-(3,4-dichlorophenyl)-3-methoxycarbonylpropionic acid.

$[\alpha]_D^{20}$+130.0°, $[\alpha]_{436}^{20}$+222.6° (c=1.01, methanol);

$^1$H-NMR (200 MHzFT, TMS, CDCl$_3$); 2.71 (1H, dd, J=5.7, 17.4 Hz), 3.23 (1H, dd, J=9.6, 17.4 Hz), 3.70 (3H, s), 4.02 (1H, dd, J=5.7, 9.6 Hz), 7.13 (1H, dd, J=2.2, 8.4Hz), 7.39 (1H, d, J=2.2 Hz), 7.41 (1H, d, J=8.4 Hz).

Part of the obtained crystals were methylesterified by adding trimethylsilyldiazomethane at room temperature to obtain dimethyl 2-(3,4-dichlorophenyl)succinate. HPLC anlaysis using an optically active column (CHIRALCEL OD, Dicel Chemical Industries Co., Ltd.) showed that this substance had an optical purity (e.e.) of 97.8%.

EXAMPLE 27

Synthesis of Optically Active 3-(3,4-Dichlorophenyl)-3-ethoxycarbonylplropionicl Aicd·(S)-1-phenylethylamine Salt 1.22 g (10.1 mmol) of (−)-1-phenylethylamine, 0.0767 g (0.504 mmol) of DBU and 24.7 ml of 2-propanol were added to 2.91 g (10.0 mmol) of (±)-3-(3,4-dichlorophenyl )-3-ethoxycarbonylpropionic acid, and the mixture was refluxed under heating and then cooled till the internal temperature became 72° C. With this temperature maintained, the solution was stirred in a suspended state for 8 hours, then cooled to an internal temperature of 20° C. and stirred at this temperature for 0.5 hour. The precipitated crystals were filtered out, washed-with a small quantity of 2-propanol and dried to give 3.42 g (82.9% yield) of optically active 3-(3,4-dichlorophenyl)-3-ethoxycarbonylpropionic acid·(S)-1-phenylethyamine salt.

$^1$H-NMR (200 MHzFT, TMS, CD$_3$OD); 1.19 (3H, t, J=7.1 Hz), 1.60 (3H, d, J=6.9 Hz), 2.52 (1H, dd, J=6.4, 15.9 Hz), 2.95 (1H, dd, J=9.2, 15.9 Hz), 4.04 (1H, dd, J=6.4, 9.2 Hz), 4.11 (2H, q (with small coupling), J=7.1 Hz), 4.39 (1H, q, J=6.9 Hz), 7.23 (1H, dd, J=2.1, 8.3 Hz), 7.30–7.53 (7H, m).

Part of this salt was methyl-esterified by adding trimethylsilyldiazomethane at room temperature to obtain ethylmethyl 2-(3,4-dichlorophenyl)succinate. HPLC analysis using an optically active column (CHIRALCEL OD, Dicel Chemical Industries Co., Ltd.) showed that this substance had an optical purity (e.e.) of 68.4%.

The salt recovered by removing the solvent from the filtrate and washings containing the optically active 3-(3,4-dichlorophenyl)-3-ethoxycarbonylpropionic acid·(S)-1-phenylethylamine salt had an optical purity (e.e.) of 64.7%.

EXAMPLE 28

Synthesis of 3-(3,4-Dichlorophenyl)-3-methoxycarbonylpropionic Acid·(S)-1-(p-tolyl) ethylamine Salt In the procedure of Example 11, (S)-1-(p-tolyl) ethylamine was used in place of (S)-1-phenylethylamine and a 2-propanol/isopropyl ether mixture was used as the solvent to obtain the title salt in a yield of 88.2%.

$^1$H-NMR (200 MHzFT, TMS, CDCl$_3$); 1.58 (3H, d, J=6.8 Hz), 2.34 (3H, s), 2.51 (1H, dd, J=6.4, 16.0 Hz), 2.94 (1H, dd, J=9.2, 16.0 Hz), 3.64 (3H, s), 4.05 (1H, dd, J=6.4, 9.2 Hz), 4.36 (1H, q, J=6.8 Hz), 7.17–7.50 (7H, m).

EXAMPLE 29

Synthesis of 3-(3,4-Dichlorophenyl)-3-methoxycarbonylpropionic Acid·(R)-1-(1-naphthyl) ethylamine Salt In the procedure of Example 11, (R)-1-(1-naphthyl) ethylamine was used in place of (S)-1-phenylethylamine and 2-propanol was used as the solvent to obtain the title salt in a yield of 79.7%.

$^1$H-NMR (200 MHzFT, TMS, CDCl$_3$); 1.73 (3H, d, J=6.7 Hz), 2.51 (1H, dd, J=6.3, 16.0 Hz), 2.95 (1H, dd, J=9.2, 16.0 Hz), 3.65 (3H, s), 4.05 (1H, dd, J=6.3, 9.2 Hz), 5.34 (1H, q, J=6.7 Hz), 7.22 (1H, dd, J=2.1, 8.4 Hz), 7.38–7.70 (6H, m), 7.87–8.00 (2H, m), 8.13 (1H, br d, J=8.3 Hz).

EXAMPLE 30

Synthesis of 3-(3,4-Dichlorophenyl)-3-methoxycarbonylpropionic Acid·(S)-1-phenyl-2-(p-tolyl)ethylamine Salt In the procedure of Example 11, (S)-1-phenyl-2-(p-tolyl) ethylamine was used in place of (S)-1-phenylethylamine and an n-octane/2-propanol mixture was used the solvent to obtain the title salt in a yield of 94.6%.

¹H-NMR (200 MHzFT, TMS, CDCl₃); 2.26 (3H, s), 2.53 (1H, dd, J=6.4, 16.0 Hz), 2.96 (1H, dd, J=9.2, 16.0 Hz), 3.10 (1H, dd, J=8.7, 13.5 Hz), 3.22 (1H, dd, J=6.6, 13.5 Hz), 3.65 (3H, s), 4.06 (1H, dd, J=6.4, 9.2 Hz), 4.41 (1H, dd, J=6.6, 8.7 Hz), 6.90–7.10 (4H, m), 7.16–7.52 (8H, m).

EXAMPLE 31

Synthesis of 3-(3,4-Dichlorophenyl)-3-methoxycarbonylpropionic Acid·(S)-N-benzyl-1-phenylethylamine Salt In the procedure of Example 11, (S)-N-benzyl-1-phenylethylamine was used in place of (S)-1-phenylethylamine and an n-octane/2-propanol mixture was used as the solvent to obtain the title salt in a yield of 85.6%.

¹H-NMR (200 MHz, CDCl₃); 1.62 (3H, d, J=6.9 z), 2.56 (1H, dd, J=6.3, 16.2 Hz), 2.98 (1H, dd, J=9.2, 16.2 Hz), 3.65 (3H, s), 3.83, 3.97 (2H, ABq, J=13.1 Hz), 4.07 (1H, dd, J=6.2, 9.2 Hz), 4.27 (1H, q, J=6.9 Hz), 7.24 (1H, dd, J=2.1, 8.3 Hz), 7.28–7.52 (12H, m).

EXAMPLE 32

Synthesis of (+)-3-(3,4-Dichlorophenyl)-3-benzyloxycarbonylpropionic Acid·(S)-1-phenylethylamine Salt 176.60 g (0.500 mol) of 3-(3,4-dichlorophenyl)-3-benzyloxycarbonylpropionic acid was suspended in 1,250 ml of 2-propanol and the solution was heated to an internal temperature of 70° C. Then 60.59 g (0.500 mol) of (S)-1-phenylethylamine and 6.09 g (0.040 mol) of DBU were added and the solution was heated to an internal temperature of 75° C. and stirred. With this temperature maintained, the solution was further stirred for 3 hours, then cooled slowly to an internal temperature of 30° C. and additionally stirred at this temperature for 2 hours. The precipitated crystals were filtered by a Nutsche funnel and then washed thrice with 250 ml of 2-propanol to obtain 177.40 g (72.9% yield) of (+)-3-(3,4-dichlorophenyl)-3-benzyloxycarbonylpropionic acid·(S)-1-phenylethylamine salt.

Part of this salt was subjected to HPLC analysis using an optically active column (CHIRALCEL OJ, Dicel Chemical Industires Co., Ltd.) to find that this substance had an optical purity (e.e.) of 99%.

¹H-NMR (200 MHzFT, TMS, CD₃OD); 1.59 (3H, d, J=6.8 Hz), 2.54 (1H, dd, J=6.4, 16.0 Hz), 2.98 (1H, dd, J=9.2, 16.0 Hz), 4.11 (1H, dd, J=6.4, 9.1 Hz), 4.38 (1H, q, J=6.8 Hz), 5.11 (2H, s), 7.18–7.32 (6H, m), 7.36–7.48 (7H, m).

EXAMPLE 33

Synthesis of (+)-3-(3,4-Dichlorophenyl)-3-benzyloxycarbonyl Acid 157.22 g (0.323 mol) of (+)-3-(3,4-dichlorophenyl)-3-benzyloxycarbonylpropionic acid·(S)-1-phenylethylamine salt was suspended in 1,292 ml of ethyl acetate, and with the internal temperature adjusted to 25° C., 355 ml (0.355 mol) of 1N hydrochloric acid was added dropwise over a period of 30 minutes. Then the solution was stirred for 10 minutes and separated, and the organic layer was washed with 1,300 ml of water, further washed with 1,300 ml of a 10% saline solution and then concentrated under reduced pressure to obtain 116.34 g (0.323 mol, 100% yield) of the objective title compound. Part of this salt was subjected to HPLC analysis using an optically active column (CHIRALCEL OJ, Dicel Chemical Industries Co., Ltd.) to find that this compound had an optical purity (e.e.) of 99%. $[\alpha]_D^{25}$+40.8°, $[\alpha]_{436}^{25}$+87.9° (c=1, methanol).

EXAMPLE 34

Synthesis of (±)-10-Amino-2-[3-(3,4-dichlorophenyl)-3-methoxycarbonyl-1-oxopropyl]-1,2,3,4,6,7,8,9-octahydrobenzor[b][1,6]-3-naphthyridine To a suspension of 3-(3,4-dichlorophenyl)-3-methoxycarbonylpropionic acid (1.47 g, 5.31 mmol) in toluene (5.3 ml), a catalytic amount of dimethylformamide (20.6 μM) was added. Under cooling with ice water, oxalyl chloride (0.56 ml, 6.37 mmol) was added and the solution was stirred at room temperature for 2 hours. To the reaction solution, oxalyl chloride (2.28 ml, 3.18 mmol) was further added and the solution was further stirred for 2 hours. The reaction solution was concentrated and diluted with toluene (5 ml) to form an acid chloride solution.

Meanwhile, triethylamine (0.89 ml, 6.37 mmol) was added to a dimethylformamide (7.5 ml) solution of 10-amino-1,2,3,4,6,7,8,9-octahydrobenzo[b][1,6]-naphthyridine (1.079 g, 5.31 mmol), and the above acid chloride solution was added thereto under cooling with ice water. The solution was stirred at room temperature for 4 hours. Water was added to the reaction solution and the solution was extracted twice with ethyl acetate. The obtained organic layer was washed with a saturated saline solution and dried over anhydrous sodium sulfate, then the solvent was concentrated under reduced pressure, and the residue was purified by silica gel column chromatography (basic silica gel, 100% dichloromethane) to obtain the title compound (1.533 g, 62.4%) as a white solid.

¹H-NMR (200 MHzFT, TMS, CDCl₃), 1.76–1.92 (4H, complex), 2.35–2.48 (2H, m), 2.64–2.98 (5H, complex), 3.60–3.82 (5H, complex), 3.90–4.57 (5H, complex), 7.11–7.22 (1H, m), 7.37–7.46 (2H, m). MS (FAB, m-NBA); m/z→462, 464 [M+H]+.

EXAMPLE 35

Synthesis of (+)-10-Amino-2-[-3-(3,4-dichlorophenyl)-3-benzyloxycarbonyl-1-oxopropyl]-1,2,3,4,6,7,8,9-octahydrobenzo[b][1,6]-naphthyridine 108.08 g (0.300 mol) of (+)-3-(3,4-dichlorophenyl)-3-benzyloxycarbonylpropionic acid and 154.11 g (0.300 mol) of 10-amino-1,2,3,4,6,7,8,9-octahydrobenzo[b][1,6]-naphthyridine were suspended in 600 ml of tetrahydrofuran, and the solution was cooled to an internal temperature of 20° C. Then 127.50 g (0.126 mol) of triethylamine was added at an internal temperature of 30° C. or below over a period of 15 minutes and the solution was further cooled to an internal temperature of 20° C., after which 210.00 g (0.330 mol) of a 50% ethyl acetate solution of T3P was added dropwise at an internal temperature of 25° C. over a period of 20 minutes and the solution was stirred at this temperature for 2 hours. The internal temperature of the solution was lowered to 20° C., then 1,200 ml of water was added dropwise at an internal temperature of 25° C. over a period of 10 minutes, and the precipitated crystals were centrifugally filtered by a centrifuge and washed twice with 360 ml of a 1/2 mixture of THF and water to obtain 271.48 g (100% yield) of the title compound.

HPLC analysis using an optical active column (SUMICHIRAL OA-4400, Sumitomo Chemicals Analysis Center, Ltd.) of part of this compound showed that it had an optical purity (e.e.) of 98%.

$^1$H-NMR (200 MHzFT, TMS, CDCl$_3$), 1.75–1.95 (4H, complex), 2.38–2.43 (4H, m), 2.62–2.99 (6H, complex), 3.32 (1H, dd, J=10.1, 16.3 Hz), 3.72 (2H, t, J=5.9 Hz), 4.45 (2H, s), 5.13 (2H, d, J=2.2 Hz), 7.11–7.42 (8H, complex). MS (FAB, m-NBA); m/z→538, 540, 542 [M+H]+. $[\alpha]_D^{25}$+34.7°, $[\alpha]_{436}^{25}$+72.6° (C=0.5, tetrahydrofuran).

EXAMPLE 36

Synthesis of (±)-10-Amino-2-[3-(3,4-dichlorophenyl)-3-carboxyl-1-oxopropyl]-1,2,3,4,6,7,8,9-octahydrobenzo[b][1,6]-naphtyridine (±)-10-amino-2-[3-(3,4-dichlorophenyl)-3-methoxycarbonyl-1-oxopropyl]-12,3,4,6,7,8,9-octahydrobenzo[b][1,6]-naphthyridine (1.533 g, 3.3 mmol) was dissolved in a mixed solvent of tetrahydrofuran (20 ml) and methanol (20 ml), to which a 1N medium hydroxide solution (3.96 ml, 3.96 mmol) was added under cooling with ice water and the mixed solution was stirred at room temperature for 5 hours. After neutralized with 1N hydrochloric acid, the reaction solution was concentrated under reduced pressure, ethanol was added to the residue, the insolubles were filtered out, and the organic layer was concentrated under reduced pressure to obtain the objective title compound (1.445 g, 98%) as a light pink solid.

$^1$H-NMR (200 MHzFT, TMS, CD$_3$OD), 1.70–2.03 (4H, complex), 2.38–3.22 (8H, complex), 3.72–4.73 (6H, complex), 7.18 (1H, d, J=1.1 Hz), 7.27–7.57 (2H, complex), MS (FAB, m-NBA); m/z→448, 450 [M+H]+.

EXAMPLE 37

Synthesis of (−)-10-Amino-2-[3-(3,4-dichlorophenyl)-3-carboxyl-1-oxopropyl]-1,2,3,4,6,7,8,9-octahydrobenzo[b][1,6]-naphthyridine 271.48 g (0.300 mol) of (+)-10-amino-2-[3-(3,4-dichlorophenyl)-3-benzyloxycarbonyl-1-oxopropyl]-1,2,3,4,6,7,8,9-octahydrobenzo[b][1,6]-naphthyridine and 3,000 ml of methanol were supplied into a 5-litre autoclave. After adjusting the internal temperature to 25° C., a suspension of 1.60 g of palladium black powder in 80 ml of water was added. The autoclave atmosphere was replaced thrice with nitrogen (5 kg/cm$^2$) and then with hydrogen (8~10 kg/cm$^2$), and the solution was stirred at an internal temperature of 25° C. for about 1.5 hour. After additional three times of replacement with nitrogen (5 kg/cm$^2$), the solution was transferred into a 5-litre flask. The inside of the autoclave was washed twice with 200 ml of methanol and the washings were similarly transferred into the 5-litre flask. The solids were filtered out by a Nutsche funnel and washed with 600 ml of methanol, then with 100 ml of tap water, and the filtrate was concentrated under reduced pressure to obtain a crude product. Then 300 ml of methanol was added and the solution was heated to an internal temperature of 80° C. and stirred for one hour. Thereafter, the solution was cooled to an internal temperature of 25° C. and the precipitated crystals were filtered out by a Nutsche funnel and washed twice with 60 ml of a 1/1 mixture of methanol and water to obtain crude crystals. 300 ml of THF was added to the crude crystals, the suspension was stirred at an internal temperature of 25° C. for one hour, and the precipitated crystals were filtered out by a Nutsche funnel and washed twice with 60 ml of THF to obtain 111.71 g (76.4% yield) of the title compound.

HPLC analysis using an optically active column (SUMICHIRAL OA-4400, Sumitomo Chemicals Analysis Center, Ltd.) showed that this compound had an optical purity (e.e.) of 99%. $[\alpha]_D^{25}$−38.9°, $[\alpha]_{436}^{25}$−97.4° (c=1, methanol).

EXAMPLE 38

Synthesis of (±)-10-Amino-2-[3-(3,4-dichloroiphenyl)-4-methylamino-1,4-dioxobutyl]-1,2,3,4,6,7,8,9-octahydrobenzo[b][1,6]-naphthyridine (±)-10-amino-2-[3-(3,4-dichlorophenyl)-3-carboxyl-1-oxopropyl]-1,2,3,4,6,7,8,9-octahydrobenzo[b][1,6]-naphthyridine (100 mg, 0.223 mmol) was dissolved in a mixed solvent of tetrahydrofuran (10 ml) and dichloromethane (4 ml), to which triethylamine (31.1 µl, 0.726 mmol) was added and the reaction solution was cooled to −25° C. Then ethyl chloroformate (21.3 µl, 0.223 mmol) was added and the solution was stirred for one hour. A 40% aqueous solution of methylamine was added to the reaction solution and stirred under cooling with ice water for 30 minutes. Water was added to the reaction solution and the solution was extracted with ethyl acetate. The obtained organic layer was dried over anhydrous sodium sulfate and concentrated under reduced pressure. The residue was purified by silica gel column chromatography (basic silica gel, dichloromethane/methanol=20/1) to obtain the title compound (63.8 mg, 62%) as a light yellow solid.

$^1$H-NMR (200 MHzFT, TMS, CDCl$_3$), 1.78–1.89 (4H, complex), 2.31–2.51 (2H, m), 2.55–3.02 (8H, complex), 4.29–3.69 (2H, m), 3.69–3.85 (1H, m), 3.95–4.14 (3H, complex), 5.28–4.58 (2H, complex), 7.18–7.52 (3H, complex), MS (FAB, m-NBA); m/z→461, 463 [M+H]+.

EXAMPLE 39

Synthesis of (±)-10-Amino-2-[4-(N-methyl)amino-3-(3,4-dichlorophenyl)butyl]-1.2,3,4,6,7,8,9-octahydrobenzo[b][1,6]-naphthyridine A tetrahydrofuran solution (1 ml) of (±)-10-amino-2-[3-(3,4-dichlorophenyl)-4-methylamino-1,4-dioxobutyl]-1,2,3,4,6,7,8,9-octahydrobenzo[b][1,6]-naphthyridine (55 mg, 0.119 mmol) was added to a tetrahydrofuran solution (0.92N, 2.59 ml, 2.38 mmol) of a borane-tetrahydrofuran complex under cooling with ice water, and the solution was stirred for one hour and then refluxed under heating for 2 hours. The reaction solution was again cooled with ice water, then methanol (2 ml) was added thereto with case, and the solution was stirred for one hour. The reaction solution was concentrated under reduced pressure and the residue was dissolved in tetrahydrofuran (1 ml), to which 4N hydrogen chloride/dioxane (2 ml) was added under cooling with ice water with care and the mixture was refluxed under heating for one hour. The reaction solution was concentrated and the residue was neutralized with a sodium hydroxide solution and extracted with dichloromethane. The obtained organic layer was dried over anhydrous sodium sulfate and concentrated under reduced pressure, and the residue was purified by silica gel column chromatography (basic silica gel, dichloromethane/methanol=40/1) to obtain the title compound (37.9 mg, 74%) as a colorless oil.

$^1$H-NMR (200 MHzFT, TMS, CDCl$_3$), 1.40–2.14 (7H, complex), 2.25–2.53 (7H, complex), 2.58–2.97 (9H, complex), 3.18–3.38 (2H, m), 3.83 (2H, br, s), 7.07 (1H, dd, J=2.0, 8.2 Hz), 7.32 (1H, d, J=2.0 Hz), 7.38 (1H, d, J=8.2 Hz). MS (FAB, m-NBA); m/z→433, 435 [M+H]+.

EXAMPLE 40

Synthesis of (−)-10-Amino-2-[4-(N-benzoyl-N-methyl)-amino-3-(3,4-dichlorophenyl)butyl]-1,2,3,4,6,7,8,9-octahydrobenzo[b][1,6]-naphthyridine Salt 34.05 g (0.900 mol) of sodium borohydride was suspended in 1,440 ml of tetrahydrofuran and the suspension was cooled to an internal temperature of about 10 to 20° C., to which 170.32 g (1.200 mol) of a boron trifluoride/diethyl ether complex was added dropwise in a stream of nitrogen over a period of 20 minutes while maintaining the internal temperature at 10 to 20° C. Then the suspension was stirred at an internal temperature of 10 to 20° C. for about one hour and, with the internal temperature kept at around 10 to 20° C., 55.36 g (0.120 mol) of (+)-10-amino-2-[3-(3,4-dichlorophenyl)-4-methylamino-1,4-dioxobutyl]-1,2,3,4,6,7,8,9-octahydrobenzo[b][1,6]-naphthyridine was added in a stream of nitrogen over a period of 10 minutes, after which the mixture was heated to an internal temperature of approximately 65° C. and stirred under reflux for 8 hours. Then the solution was cooled to an internal temperature of about 0 to 10° C., and 600 ml of water was added dropwise over a period of 15 minutes while maintaining the internal temperature at 10 to 25° C., followed by the dropwise addition of 240 ml (0.720 mol) of 3N hydrochloric acid over a period of 5 minutes with the internal temperature kept at 15 to 20° C. Thereafter, the mixture was heated to an internal temperature of about 65° C., stirred under reflux for 1.5 hour and then cooled to an internal temperature of about 5 to 15° C. Then 360 ml (2.160 mol) of a 6N sodium hydroxide solution was added dropwise over a period of 20 minutes while maintaining the internal temperature at 15° C. or below, followed the dropwise addition of 20.90 ml (0.180 mol) of benzoyl chloride over a period of 5 minutes with the internal temperature kept at 15° C. or below, and then the suspension was stirred at an internal temperature of 20 to 30° C. for 2 hours. 1,200 ml of water and 1,200 ml of ethyl acetate were added, and after one-hour stirring, the liquid was separated. The organic layer was washed with 1,200 ml of a 10% saline solution and concentrated under reduced pressure. 600 ml of acetone was added to the residue and the mixture was stirred at an internal temperature of 20 to 30° C. for 2 hours. The insoluble solids were filtered out and washed twice with 120 ml of acetone. The filtrate was put into a 2-litre 4-necked flask and heated to an internal temperature of about 50 to 55° C., to which an acetone solution (240 ml) of 27.86 g (0.240 mol) of maleic acid was added drop-wise over a period of 45 minutes. Then 600 ml of acetone was added and the suspension was stirred at an internal temperature of 50 to 55° C. for one hour, then cooled to an internal temperature of 20 to 30° C. and stirred for 30 minutes. The precipitated crystals were filtered out by a Nutsche funnel to obtain crude crystals. 1,200 ml of 2-propanol was added to these crude crystals and the suspension was heated to an internal temperature of about 80 to 85° C. and stirred for about one hour, then cooled to an internal temperature of about 20 to 30° C. and further stirred for 30 minutes. The precipitated crystals were filtered out by a Nutsche funnel and washed twice with 120 ml of 2-propanol to obtain 72.58 g (78.0% yield) of a maleate of the title compound.

Part of this salt was subjected to HPLC analysis using an optically active column (CHIRALCEL OD-R, Dicel Chemical Industries Co., Ltd.) to find that this compound had an optical purity (e.e.) of 99%. $[\alpha]_D^{25}$ −27.8°, $[\alpha]_{436}^{25}$ −62.3° (c=1, methanol).

EXAMPLE 41

Synthesis of 4-Ethoxycarbonylamino-3-(3,4-dichlorophenyl)butyric Acid

Ethyl chloroformate (3.19 g, 29.4 mmol) was added to a 2N sodium hydroxide solution (26.3 ml, 52.4 mmol) of 4-amino-3-(3,4-dichlorophenyl)butyric acid (5.61 g, 22.6 mmol) under cooling with ice water and the mixture was stirred at 0° C. for 30 minutes and then at room temperature for 4 hours. The reaction solution was washed with diethyl ether and the aqueous layer was adjusted to a pH of about 2 with 1N hydrochloric acid and extracted with diethyl ether. The organic layer was dried over anhydrous sodium sulfate and concentrated under reduced pressure to obtain the title compound (7.23 g, quant.) as a light brown oily substance.

$^1$H-NMR (200 MHzFT, TMS, CDCl$_3$), 1.20 (3H, t, J=7.0 Hz), 1.52–2.82 (2H, m), 3.22–3.57 (3H, complex), 4.08 (2H, q, J=7.1 Hz), 4.71 (1H, br, s), 6.12 (1H, br, s), 7.06 (1H, dd, J=2.0, 8.4 Hz), 7.31 (1H, d, J=2.0 Hz), 7.40 (1H, d, J=8.3 Hz). MS (FAB, m-NBA); m/z→320 [M+H]+.

EXAMPLE 42

Synthesis of (±)-10-Amino-2-[4-(N-ethoxycarbonyl)amino-3-(3,4-dichlorophenyl)-1-oxobutyl]-1,2,3,4,6,7,8,9-octahydrobenzo[b][1,6]-naphthyridine 10-amino-1,2,3,4,6,7,8,9-octahydrobenzo[b][1,6]-naphthyridine (1 g, 4.92 mmol) and 4-ethoxycarbonylamino-3-(3,4-dichlorophenyl)butyric acid (1.73 g, 5.41 mmol) were dissolved in a mixed solvent of dimethylformamide (5 ml) and tetrahydrofuran (5 ml). To this solution were added 1-hydroxybenzotriazole (798 mg, 5.9 mmol) and N-ethyl-N'-3-dimethylaminopropylcarbodiimide (1.13 g, 5.9 mmol), and the mixture was stirred overnight at room temperature. Water was added to the reaction solution and the solution was extracted thrice with dichloromethane. The obtained organic layer was washed with a saturated sodium hydrogencarbonate solution, dried over anhydrous sodium sulfate and concentrated, and the residue was purified by silica gel column chromatography (basic silica gel, dichloromethane/methanol=50/1) to obtain the objective title compound (1.17 g, 47%) as a white solid.

$^1$H-NMR (200 MHzFT, TMS, CDCl$_3$), 1.12–1.26 (3H, m), 1.77–1.92 (4H, complex), 2.35–2.49 (2H, m), 2.65–2.92 (6H, complex), 3.30–3.75 (5H, complex), 3.85–4.19 (4H, complex), 4.84 (1H, br, s), 6.99–7.41 (3H, complex), MS (FAB, m-NBA); m/z→505, 507 [M+H]+.

EXAMPLE 43

Synthesis of (±)-10-Amino-2-[4-(N-ethoxycarbonyl)amino-3-(3,4-dichlorophenyl)-1-oxobutyl]-1,2,3,4-tetrahydrobenzo[b][1,6]-naphthyridine The title compound was obtained by the same procedure as in Example 42.

$^1$H-NMR (200 MHzFT, TMS, CDCl$_3$), 1.11–1.26 (3H, m), 2.67–3.15 (4H, complex), 3.29–3.90 (5H, complex), 4.05 (2H, q, J=7.1 Hz), 4.42–4.90 (5H, complex), 7.00–8.03 (7H, complex). MS (FAB, m-NBA); m/z→501, 503 [M+H]+.

EXAMPLE 44

Synthesis of 2-[(±)-4-(N-Ethoxycarbonyl)amino-3-(3,4-dichlorophenyl)-1-oxobutyl]-1,2,3,4,6,7,8,9-octahydrobenzo[b][1.6]-naphthyridine The title compound was obtained by the same procedure as in Example 42.

$^1$H-NMR (200 MHZFT, TMS, CDCl$_3$), 1.12–1.23 (3H, m), 2.60–3.05 (8H, complex), 3.31–3.75 (5H, complex), 3.91–4.12 (2H, m), 4.29–4.73 (2H, m), 4.78–4.99 (1H, m), 6.91–7.45 (4H, complex). MS (FAB, m-NBA); m/z→490, 492 [M+H]+.

EXAMPLE 45

Synthesis of (±)-10-Amino-2-[4-(N-methyl)amino-3-(3,4-dichlorophenyl)butyl]-1,2,3,4,6,7,8,9-octahydrobenzo[b][1.6]-naphthyridine Lithium aluminum hydride (259 mg, 6.83 mmol) was suspended in tetrahydrofuran (1 ml) in a nitrogen atmosphere, to which a tetrahydrofuran (5 ml) solution of (±)-10-amino-2-[4-(N-ethoxycarbonyl)amino-3-(3,4-dichlorophenyl)-1-oxobutyl]-1,2,3,4,6,7,8,9-octahydrobenzo[b][1,6]-naphthyridine (1.15 g, 2.28 mmol) was added and the solution was stirred at room temperature for 30 minutes and then refluxed under heating for 2.5 hours. The reaction solution was cooled to room temperature, and a saturated sodium sulfate solution (1 ml) was added thereto with care under cooling with ice water and stirred at room temperature for one hour. To the reaction solution were added anhydrous sodium sulfate (1 g) and cerite (1 g), and the solution was further stirred for one hour. Cerite was filtered out and the organic layer was concentrated under reduced pressure to obtain the title compound (997 mg, quant.) as a light yellow amorphous substance.

The determined values of $^1$H-NMR and MS (FAB, m-NBA) agreed with those of Example 39.

EXAMPLE 46

Synthesis of (±)-2-[4-(N-Methyl)amino-3-(3,4-dichlorophenyl)butyl]-1,2,3,4,6,7,8,9-octahydrobenzo[b](1,6)-naphthyridine The title compound was obtained by the same procedure as in Example 45.

$^1$H-NMR (200 MHzFT, TMS, CDCl$_3$), 1.61–2.04 (6H, complex), 2.16–2.50 (5H, complex), 2.56–3.02 (11H, complex), 3.36–3.58 (2H, m), 6.96 (1H, s), 7.03–7.42 (3H, complex). MS (FAB, m-NBA); m/z→418, 420 [M+H]+.

EXAMPLE 47

Synthesis of 10-Amino-2-benzyl-1,2,3,4-tetrahydrobenzo[b][1.6]naphthyridine 11.55 g (97.80 mmol) of 2-aminobenzonitrile and 24.07 g (127.14 mmol) of N-benzylpiperidine-4-one were dissolved in 200 ml of ethyl acetate, to which 50.00 g (225.00 mmol) of trimethylsilyltrifluoromethane sulfonate was added dropwise at room temperature. After the end of the dropwise addition, the mixture was refluxed under heating for 6 hours. After air cooling, the produced crystals were filtered out and washed with 320 ml of ethyl acetate. The obtained crystals were dried, added to a mixed solution of 400 ml of water and 200 ml of ethanol and dissolved by heating. After air cooling, 250 ml of a 1N sodium hydroxide solution was added thereto and the mixture was extracted with ethyl acetate. The organic layer was washed with a saturated saline solution and dried over anhydrous sodium sulfate, and then the drying agent was filtered out. The filtrate was concentrated under reduced pressure and the residue was suspended in a mixed solution of 200 ml of ethyl acetate and 200 ml of hexane. The produced crystals were filtered out and further washed with the above mixed solution to obtain the title compound (27.39 g, 95% yield).

$^1$H-NMR (200 MHzFT, TMS, CDCl$_3$), 2.91 (1H, t, J=5.8 Hz), 3.16 (2H, t, J=5.7 Hz), 3.58 (2H, s), 3.81 (2H, s), 4.50 (2H, brs), 7.2–7.5 (6H, m), 7.59 (1H, dt, J=1.3 Hz, 6.8 Hz), 7.67 (1H, d, J=8.0 Hz), 7.90 (1H, d, J=8.4 Hz). MS (FAB); m/z 290 [M+H]+.

The methods of producing pharmaceutical preparations using the compounds obtained according to the present invention are described below concretely by showing the examples.

PREPARATION EXAMPLE 1

Injection

Purified water was added to 30 parts by weight of a novel naphthyridine derivative of the present invention and 18 parts by weight of common salt (glucose: 100 parts by weight) to make the total amount 2,000 parts by weight. After the said materials were dissolved, the solution was sterilized and filtered by Millipore Filter Type GS (registered trade name). 2 g of the filtrate was pipetted into a vial and the vial was capped and rolled to obtain an injection containing 30 mg of a compound of the present invention.

PREPARATION EXAMPLE 2

Tablet 10 parts by weight of a novel naphthyridine derivative of the present invention, 30 parts by weight of potato starch, 150 parts by weight of crystal lactose, 108 parts by weight of crystal cellulose and 2 parts by weight of magnesium stearate were mixed by a V type mixer, and the mixture was compressed into tablets, each tablet weighing 60 mg and containing 2 mg of a compound of the present invention.

The physiological activity of the compounds obtained according to the process of the present invention is explained below in the concrete by showing the test examples.

TEST EXAMPLE 1

NK-2 Receptor Binding Test

The duodenum taken out from a Fischer-strain male rat was homogenized in a 50 mM tris-hydrochloride buffer solution containing ethylenediaminetetracetic acid (1 mM), and 48,000 g of the obtained homogenate was subjected to centrifugal sedimentation at 4° C. for 20 minutes. The produced pellets were washed thrice with 10 times as much volume of a 50 mM trishydrochloride butter solution containing KCl (300 mM) and ethylenediaminetetracetic acid (10 mM), and the obtained membrane preparation was suspended in 10 times as much volume of a 50 mM tris-hydrochloride buffer solution (pH 7.4) and kept at −80° C. till it was offered to use. The above membrane preparation (20 mg/ml) was incubated with a radioactive legand 125 I-neurokinin A ($1\times10^{-9}$ M) in a 50 mM tris-hydrochloride buffer solution (pH 7.4) containing bovine serum albumin (10 mg/ml), bacitracin (40 μg/ml), leupepsin (4 μg/ml), chymostatin (50 μg/ml), antipain ($1\times10^{-4}$ M) and MnCl$_2$ (1 mM) in the presence of a drug or its solvent at room temperature for 90 minutes. The reaction solution was suction-filtered by a GE/B filter pretreated with polyethylene-imine (0.1%), and was washed with 3 ml of a 50 mM tris-hydrochloride buffer solution (pH 7.4) containing MnCl$_2$ (1 mM), and the radioactivity in the filter was measured by a gamma counter. With the radioactivity in the presence of Nle10 eurokinin A (4–10) ($3\times10^{-6}$ M) being taken as non-specific binding, the specific binding inhibition rate by the drug was given as control in the case of a solvent, and the 50% inhibition concentration (IC50) of the drug was determined from the linear regression. The obtained results are shown in Table 2.

TABLE 2

| Compound No. | IC50 (M) |
|---|---|
| ②-b | $5.6 \times 10^{-8}$ |
| ③-b | $7.0 \times 10^{-8}$ |
| ⑥-b | $1.8 \times 10^{-8}$ |

IC 50 of the drug against radioactive neurokinin A binding

As is apparent from Table 2, the novel naphthyridine derivatives of the present invention are capable of inhibiting binding of neurokinin A to NK-2 receptor with a very low concentration and have a strong inhibitory action against binding of endogenous stimulants to NK-2 receptor.

TEST EXAMPLE 2
Antagonistic Action Against NK-2 Receptor

A Hartley-strain male guinea pig was caused to die by head contusion and blood depletion, and its trachea was extracted. Specimens were prepared by joining 5 slices from said trachea, and they were suspended with a tension of 0.5 gram-weight in a 15-ml Magunus tank containing a 37° C. Krebs-Henseleit liquid through which a mixed gas of 95% $O_2$ and 5% $CO_2$ had been passed. A Krebs-Henseleit liquid containing indomethacin ($5 \times 10^{-6}$ M) was used to obviate the participation of endogenous prostaglandin. After confirming the maximum contraction of each specimen by methacholine, a drug or its solvent was added and, after 110-minute incubation, neurokinin A ($1 \times 10^{-9}$ M) was acted thereto. Phosphoramidon ($1 \times 10^{-5}$ M) was added for inhibiting decomposition of neurokinin A 30 minutes before the addition of neurokinin A and (±) CP-96345 ($3 \times 10^{-7}$ M) was added for eliminating the participation of NK-1 receptor 20 minutes before the addition of neurokinin A. The contraction by neurokinin A was first determined as a ratio to the maximum contraction of each specimen, and then the inhibition rate by the drug was determined with the amount of contraction of the solvent-added specimen as control. Results are shown in Table 3.

TABLE 3

Inhibition of neurokinin A-induced contraction by the drug

| Compound No | Concentration (M) | Inhibition rate (%) |
|---|---|---|
| ②-b | $5 \times 10^{-9}$ | 89.1 |

As is seen from Table 3, the novel naphthyridine derivatives of the present invention show a strong inhibitory action against contraction by neurokinin A with a very low concentration and have a very strong antagonistic action against NK-2 receptor.

TEST EXAMPLE 3
Antagonistic Action Against NK-1 Receptor

A Hartley strain male guinea pig was caused to die by head contusion and blood depletion, and its ileum was extracted. An approximately 3 cm long specimen was prepared therefrom, and it was suspended with a tension of 0.5 gram-weight in a 15 ml Mogunus tank containing a 37° C. Krebs-Henseleit liquid through which a mixed gas of 95% $O_2$ and 5% $CO_2$ had been passed. A Krebs-Henseleit liquid containing atropin ($1 \times 10^{-6}$ M) and indomethacin ($5 \times 10^{-6}$ M) was used to get rid of the participation of endogenous acetylcholine and prostaglandin. Methyl Substance P ($1 \times 10^{-9}$ M), which is a specific stimulant of NK-1 receptor, was acted repeatedly at intervals of 40 minutes. After contraction by Methyl Substance P was stabilized, the drug was added in various concentrations and, after 35-minute incubation, Methyl Substance P was again acted. The contraction inhibition rate by the drug was determined with the contraction just before the addition of the drug as control, and the 50% inhibition concentration (IC50) of the drug was calculated from the linear regression. The obtained result is shown in Table 4.

TABLE 4

IC50 of the drug against contraction by Methyl Substance P

| Compound No. | IC50 (M) |
|---|---|
| ②-b | $4.7 \times 10^{-7}$ |

As is apparent from Table 4, the compounds according to the present invention have an antagonistic action against NK-1 receptor as well as against NK-2 receptor.

TEST EXAMPLE 4
Antagonistic Action Against NK-3 Receptor

A Hartley-strain male guinea pig was caused to die by head contusion and blood depletion, and its ileum was extracted. An approximately 3 cm long specimen was prepared therefrom, and it was suspended with a tension of 0.5 gram-weight in a 15 ml Magunus tank containing a 37° C. Kregs-Henseleit liquid through which a mixed gas of 95% $O_2$ and 5% $CO_2$ had been passed. A Krebs-Henseleit liquid containing atropin ($1 \times 10^{-6}$ M) and indomethacin ($5 \times 10^{-6}$ M) was used to obviate the participation of endogenous acetylcholine and prostaglandin. Senktide ($1 \times 10^{-9}$ M), which is a specific stimulant of NK-3 receptor, was acted repeatedly at intervals of 50 minutes. After contraction by senktide was stabilized, the drug was added in various concentrations and, after 35-minute incubation, senktide was again acted. The contraction inhibition rate by the drug was determined with the amount of contraction just before the addition of the drug as control, and the 50% inhibition concentration (IC50) of the drug was determined from the linear regression. The obtained result is shown in Table 5.

TABLE 5

IC50 of the drug against contraction by senktide

| Compound No. | IC50 (M) |
|---|---|
| ②-b | $1.8 \times 10^{-7}$ |

As is apparent from Table 5, the compounds of the present invention have an antagonistic action against NK-3 receptor, too.

TEST EXAMPLE 5
Inhibitory Action Against Stricture of Airway

The non-treated Hartley strain male guinea pigs and the Hartley strain male guinea pigs which had been actively sensitized by subcutaneous administration of 300 mg/kg of ovalbumin 14 to 21 days ago were used. A tube was inserted into the trachea of each guinea pig anesthetized with pentobarbital, and positive pressure breathing was conducted at a rate of 60 times of breathing per minute (10 ml/kg) by an artificial breathing system. Lateral pressure of the tube in the trachea was measured as an index of stricture of airway. Spontaneous respiration was inhibited by the administration of succinylcholine. To the non-treated guinea pigs, 2 μmol of Nle10 neurokinin A (4–10)—a specific stimulant to NK-2 receptor—was intravenously injected repeatedly at intervals of 10 minutes. After the induced airway restriction reaction was stabilized, the drug was administered intravenously or perorally. 3 minutes after intravenous administration or 50 minutes after peroral or intraduodenal administration, Nle10 neurokinin A (4–10) was again intravenously injected. The inhibition rate by the drug was determined with the degree of airway restriction before drug administration as control.

15 minutes after intravenous administration of 4.6 μmol/kg of phosphoramidon to each actively sensitized guinea pig, it was forced to inhale, for 2 minutes, an aerosol of an antigen ovalbumin solution (2 mg/ml) generated by a supersonic nebulizer to induce stricture of the airway. The drug or its solvent was administered perorally 50 minutes before the antigen inhalation. 8 minutes after antigen inhalation of the solvent-administered group, the inhibition rate of the drug-administered group was determined with the degree of airway stricture of the solvent-administered group as control. Results are shown in Table 6.

TABLE 6

Inhibition rate by the drug against stricture of airway caused by NK-2 receptor stimulation and antigen inhalation

| Compound No. | Dosage (μmol/kg) | Way of administration | Inhibition rate (%) NK-2 receptor stimulation and antigen inhalation |
|---|---|---|---|
| ②-b | 1 | Intravenous | 94.2 |
| ③-b | 0.5 | Intravenous | 70.0 |
| ⑥-b | 0.5 | Intravenous | 100.0 |
| ②-b | 8 | Peroral | 67.2 |
| ⑥-b | 8 | Peroral | 81.5 |
| ②-b | 10 | Peroral | 54.1 |

As is seen from Table 6, the novel naphthyridine derivatives of the present invention show an inhibitory effect against stricture of airway at a very low dosage and have a strong anti-asthmatic action.

TEST EXAMPLE 6
Toxic Action in Mouse

Toxicity of the novel naphthyridine derivatives of the present invention was examined. Results are shown in Table 7.

TABLE 7

Toxicity by intravenous administration of the drug

| Compound No. | Dosage (μmol/kg) | Toxicity |
|---|---|---|
| ②-b | 22 | None |
|  | 65 | None |
| ⑥-b | 65 | None |

As is obvious from Table 7, the novel naphthyridine derivatives of the present invention show no toxicity even when administered at a high dose and have few side effects.

As described above, the novel naphthyridine derivatives according to the present invention have a prominent antagonistic action against the tachykinin receptors and are also well satisfactory in terms of safety.

INDUSTRIAL APPLICABILITY

According to the present invention, the novel naphthyridine derivatives, which are the compounds having a conspicuous activity as a tackykinin receptor antagonist, can be produced at high efficiency. It is also possible to produce the optically active version of the novel naphthyridine derivatives by optically resolving the novel intermediates used in the above production process.

What is claimed is:

1. A process for producing a naphthyridine derivative, which comprises carrying out a condensation reaction between a compound represented by the following formula (1):

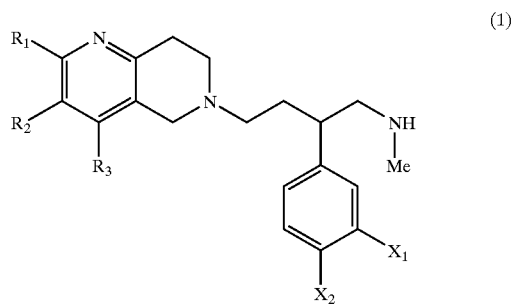

wherein $R_1$, $R_2$ and $R_3$ represent independently a hydrogen atom, a lower alkyl group, a lower alkoxyl group, an aryl group, a heteroaryl group, an amino group or a halogen atom, or $R_1$ and $R_2$ or $R_2$ and $R_3$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, aryl group, heteroaryl group, lower alkoxyl group, halogen atom and trifluoromethyl group; and $X_1$ and $X_2$ represent respectively a halogen atom, and a compound represented by the following formula (2):

wherein Y represents an aryl group which may have 1 to 3 substituents selected from halogen atom and lower alkoxyl group; and Z represents a halogen atom, a hydroxyl group, a lower alkylcarbonyloxy group or an arylcarbonyloxy group, to produce a compound represented by the following formula (3):

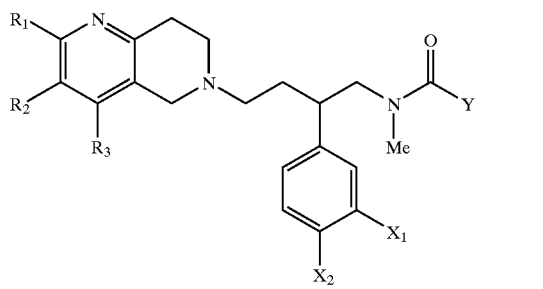

wherein $R_1$, $R_2$, $R_3$, $X_1$, $X_2$ and Y have the same meaning as defined above.

2. The process according to claim 1, wherein in the formula (1), $R_1$ and $R_2$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, lower alkoxyl group, halogen atom, aryl group, heteroaryl group and trifluoromethyl group; and $R_3$ represents a group, an aryl group, an amino group or a halogen atom.

3. The process according to claim 1, wherein in the formula (1), $R_1$ and $R_2$ are combined to form a cyclic group with the interposition of a C2–C5 alkylene group or a C2–C5 alkenylene group, which cyclic group may have a substituent selected from lower alkyl group, lower alkoxyl group, halogen atom and trifluoromethyl group; $R_3$ represents a hydrogen atom, a lower alkyl group, a lower alkoxyl group, an aryl group, an amino group or a halogen atom; and in the formula (2), Y represents a phenyl group which may have 1 to 3 substituents selected from halogen atom and lower alkoxyl group.

4. The process according to claim 1, wherein in the formula (1), $R_1$ and $R_2$ are combined to form a cyclic group with the interposition of a butylene group or a butenylene group; $R_3$ represents a hydrogen atom, an aryl group, an amino group or a halogen atom; and in the formula (2), Y represents a phenyl group.

5. A process for producing a naphthyridine derivative, which comprises acylating the amino group of a compound represented by the following formula (3)':

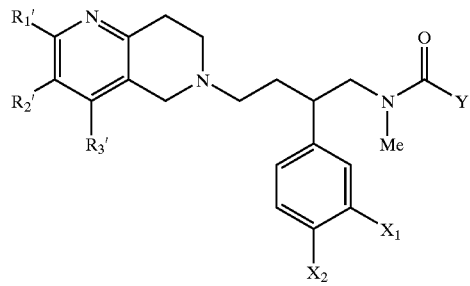

(3)' wherein $R_1'$, $R_2'$ and $R_3'$ represent independently a hydrogen atom, a lower alkyl group, a lower alkoxyl group, an aryl group, a heteroaryl group, an amino group or a halogen atom, or $R_1'$ and $R_2'$ or $R_2'$ and $R_3'$ are combined to form a cyclic group with the interposition of a saturated or unsaturated carbon-carbon bond, which cyclic group may contain 1 to 3 heteroatoms selected from nitrogen atom, oxygen atom and sulfur atom and may also have a substituent selected from lower alkyl group, aryl group, heteroaryl group, lower alkoxyl group, halogen atom and trifluoromethyl group, and at least one of $R_1'$, $R_2'$ and $R_3'$ represents an amino group; $X_1$ and $X_2$ represent respectively a halogen atom; and Y represents an aryl group which may have 1 to 3 substituents selected from halogen atom and lower alkoxyl group, to produce a compound represented by the formula (3)":

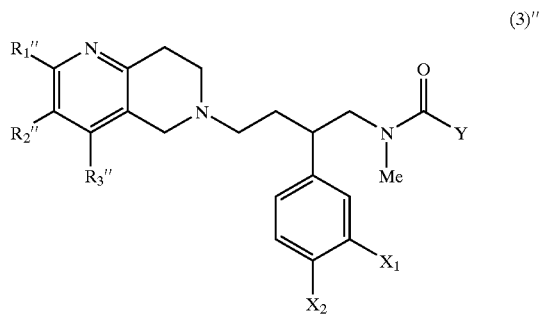

(3)"

wherein $R_1''$, $R_2''$ and $R_3''$ represent independently a hydrogen atom, a lower alkyl group, a lower alkoxyl group, an aryl group, a heteroaryl group or a halogen atom, or $R_1''$ and $R_2''$ or $R_2''$ and $R_3''$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, aryl group, heteroaryl group, lower alkoxyl group, halogen atom and trifluoromethyl group, and at least one of $R_1''$, $R_2''$ and $R_3''$ represents a lower alkylcarbonylamino group or an arylcarbonylamino group; and $X_1$ and $X_2$ are as defined above.

6. The process according to claim 5, wherein in the formula (3)', $R_1'$ and $R_2'$ are combined to form a cyclic group with the interposition of a saturated or unsaturated carbon-carbon bond, which cyclic group may contain 1 to 3 heteroatoms selected from nitrogen atom, oxygen atom and sulfur atom and may also have a substituent selected from lower alkyl group, aryl group, heteroaryl group, lower alkoxyl group, halogen atom and trifluoromethyl group; $R_3'$ represents an amino group; and in the formula (3)", $R_1''$ and $R_2''$ are combined to form a cyclic group with the interposition of a saturated or unsaturated carbon-carbon bond, which cyclic group may contain 1 to 3 hetero-atoms selected from nitrogen atom, oxygen atom and sulfur atom and may also have a substituent selected from lower alkyl group, aryl group, heteroaryl group, lower alkoxyl group, halogen atom and trifluoromethyl group; and $R_3$ represents a lower alkylcarbonylamino group or an arylcarbonylamino group.

7. The process according to claim 5, wherein in the formula (3)', $R_1'$ and $R_2'$ are combined to form a cyclic group with the interposition of a C2–C5 alkylene group or a C2–C5 alkenylene group, which cyclic group may have a substituent selected from lower alkyl group, lower alkoxyl group, halogen atom and trifluoromethyl group; $R_3'$ represents an amino group; Y represents a phenyl group which may have 1 to 3 substituents selected from halogen atom and lower alkoxyl group; and in the formula (3)", $R_1''$ and $R_2''$ are combined to form a cyclic group with the interposition of a C2–C5 alkylene group or a C2–C5 alkenylene group, which cyclic group may have a substituent selected from lower alkyl group, lower alkoxyl group, halogen atom and trifluoromethyl group; and $R_3''$ represents a lower alkylcarbonylamino group.

8. The process according to claim 5, wherein in the formula (3)', $R_1'$ and $R_2'$ are combined to form a cyclic group with the interposition of a butylene group or a butenylene group; $R_3'$ represents an amino group; Y represents a phenyl group; and in the formula (3)", $R_1''$ and $R_2''$ are combined to form a cyclic group with the interposition of a butylene group or a butenylene group; and $R_3''$ represents a lower alkylcarbonylamino group.

* * * * *